(12) United States Patent
Hwang

(10) Patent No.: US 11,589,793 B2
(45) Date of Patent: Feb. 28, 2023

(54) ELECTROCARDIOGRAM MEASUREMENT APPARATUS

(71) Applicant: HEXACHECK INC., Daejeon (KR)

(72) Inventor: In-Duk Hwang, Sejong (KR)

(73) Assignee: WELLBEINGSOFT INC., Daejeon (KR)

( * ) Notice: Subject to any disclaimer, the term of this patent is extended or adjusted under 35 U.S.C. 154(b) by 145 days.

(21) Appl. No.: 16/768,769

(22) PCT Filed: Dec. 3, 2018

(86) PCT No.: PCT/KR2018/015193
§ 371 (c)(1),
(2) Date: Jun. 1, 2020

(87) PCT Pub. No.: WO2019/108044
PCT Pub. Date: Jun. 6, 2019

(65) Prior Publication Data
US 2020/0315480 A1    Oct. 8, 2020

(30) Foreign Application Priority Data

Dec. 1, 2017 (KR) .................. 10-2017-0164602

(51) Int. Cl.
*A61B 5/332* (2021.01)
*A61B 5/00* (2006.01)
(Continued)

(52) U.S. Cl.
CPC .............. *A61B 5/332* (2021.01); *A61B 5/002* (2013.01); *A61B 5/02055* (2013.01);
(Continued)

(58) Field of Classification Search
CPC ..... A61B 5/332; A61B 5/002; A61B 5/02055; A61B 5/282; A61B 5/30; A61B 5/316;
(Continued)

(56) References Cited

U.S. PATENT DOCUMENTS

| 5,191,891 A * | 3/1993 | Righter ................ A61B 5/335 600/523 |
| 6,721,591 B2 | 4/2004 | Wei et al. |
| 7,466,148 B2 * | 12/2008 | Fridman ................ G01R 29/12 324/686 |
| 7,647,093 B2 | 1/2010 | Bojovic et al. |
| 7,870,761 B2 | 1/2011 | Valentine et al. |
| 8,903,477 B2 | 12/2014 | Berkner |

(Continued)

FOREIGN PATENT DOCUMENTS

| CN | 104490387 B | 9/2016 |
| DE | 20119965 U1 | 5/2002 |

(Continued)

OTHER PUBLICATIONS

Hwang et al. "Direct Interference Canceling 25 for Two-Electrode Biopotential Amplifier" IEEE Trans Biomed Eng. vol. 55, No. 11, pp. 2620-2627, Nov. 2008.

*Primary Examiner* — Jonathan T Kuo
(74) *Attorney, Agent, or Firm* — Maschoff Brennan

(57) ABSTRACT

The present invention relates to an electrocardiogram measurement apparatus (measurement sensor) which can be used in combination with a smartphone by an individual. The electrocardiogram measurement apparatus according to the present invention comprises: two amplifiers for receiving electrocardiogram signals from a first electrode and a second electrode; one electrode driving unit; a third electrode for receiving an output of the electrode driving unit; an A/D converter connected to an output terminal of each of the two amplifiers and converting analog signals into digital signals; a microcontroller for receiving the digital signals from the A/D converter; and a communication means for transmitting the digital signal, wherein: the microcontroller is supplied with power from a battery; the microcontroller controls the A/D converter and the communication means; and each of (Continued)

the two amplifiers amplifies one electrocardiogram signal so as to simultaneously measure two electrocardiogram signals.

17 Claims, 19 Drawing Sheets

(51) Int. Cl.
*A61B 5/0205* (2006.01)
*A61B 5/30* (2021.01)
*A61B 5/282* (2021.01)
*A61B 5/316* (2021.01)
*A61B 5/145* (2006.01)

(52) U.S. Cl.
CPC ............... *A61B 5/282* (2021.01); *A61B 5/30* (2021.01); *A61B 5/316* (2021.01); *A61B 5/681* (2013.01); *A61B 5/0006* (2013.01); *A61B 5/14532* (2013.01); *A61B 5/14546* (2013.01); *A61B 5/6826* (2013.01); *A61B 5/6838* (2013.01); *A61B 2560/0209* (2013.01); *A61B 2560/0214* (2013.01); *A61B 2562/0209* (2013.01); *A61B 2562/043* (2013.01)

(58) Field of Classification Search
CPC ............ A61B 5/681; A61B 5/0006; A61B 5/14532; A61B 5/14546; A61B 5/6826; A61B 5/6838; A61B 2560/0209; A61B 2560/0214; A61B 2562/0209; A61B 2562/043; A61B 5/308; A61B 5/7203; A61B 5/7225; A61B 5/25

See application file for complete search history.

(56) References Cited

U.S. PATENT DOCUMENTS

| | | |
|---|---|---|
| 9,962,082 B2 | 5/2018 | Kim et al. |
| 2006/0117805 A1 | 6/2006 | Valentine et al. |
| 2008/0114221 A1 | 5/2008 | Tso |
| 2009/0033440 A1 | 2/2009 | Masuda et al. |
| 2010/0076331 A1 | 3/2010 | Chan et al. |
| 2011/0306859 A1 | 12/2011 | Saldivar et al. |
| 2014/0163349 A1 | 6/2014 | Amitai et al. |
| 2015/0018660 A1 | 1/2015 | Thomson et al. |
| 2015/0327815 A1* | 11/2015 | Hwang ............... A61B 5/7278 600/547 |
| 2016/0135701 A1 | 5/2016 | Drake |
| 2016/0254003 A1 | 9/2016 | Tachibana et al. |
| 2016/0367138 A1 | 12/2016 | Kim et al. |
| 2017/0100046 A1 | 4/2017 | Roh et al. |

FOREIGN PATENT DOCUMENTS

| | | |
|---|---|---|
| JP | 2007195690 A | 8/2007 |
| KR | 10-2005-0003436 A | 1/2005 |
| KR | 10-2015-0117629 A | 10/2015 |
| KR | 10-2016-0149911 A | 12/2016 |
| KR | 10-2017-0041595 A | 4/2017 |
| WO | 2017066040 A1 | 4/2017 |

* cited by examiner

ELECTROCARDIOGRAM MEASUREMENT APPARATUS

TECHNICAL FIELD

An electrocardiography system provides a waveform of an electrical signal, namely, an electrocardiogram, which contains very useful but easily obtainable information to analyze the condition of a patient's heart. It can be said that the electrocardiography system includes an electrocardiogram measurement apparatus (a measurement sensor) and a computer. In these days, almost all individuals use a smartphone. A smartphone can be considered a computer capable of wireless communication and providing a good display. Therefore, the combination of the electrocardiogram measurement apparatus (measurement sensor) and the smartphone can be a good electrocardiography system. The present invention relates to an electrocardiogram measurement apparatus (measurement sensor) that an individual can use in association with a smartphone. According to International Patent Classification (IPC), the apparatus for measuring an electrocardiogram according to the present invention is classified into class A61B 5/04 to which detecting, measuring or recording bioelectric signals of the body or parts thereof belongs.

BACKGROUND ART

An electrocardiography system is a useful apparatus capable of conveniently diagnosing a patient's heart condition. Electrocardiography systems can be classified into several types depending on the purpose thereof. The standard of hospital electrocardiography systems which are used to obtain as much information as possible is a 12-channel electrocardiography system employing 10 wet electrodes. A patient monitoring system is used to continuously measure a patient's heart condition with a small number of wet electrodes attached to the patient's body. A Holter recorder and an event recorder that a user can use by themselves while moving around have the following essential features. These features include a compact size, battery-powered operation, a storage device provided to store measured data, and a communication device capable of transmitting the data. The Holter recorder usually uses 4 to 6 wet electrodes and cables connected to the electrodes, and provides a multi-channel ECG. However, the user feels uncomfortable about the Holter recorder because the wet electrodes connected to the cables are attached to the body. Recently released electrocardiography systems such as a patch type system also require electrodes to be kept attached to the body.

The event recorder allows users to carry the recorder and measure ECG on their own when they feel an abnormality in their heart. Therefore, the event recorder is compact and does not have a cable for connecting electrodes, and dry electrodes are provided on the surface of the event recorder. The conventional event recorder is a 1-channel electrocardiography system, i.e., a 1-lead electrocardiography system that measures one ECG signal while both hands of a user are in contact with two electrodes.

An electrocardiogram measurement apparatus which is sought or required by the present invention is required to be convenient for personal use, to provide accurate and abundant electrocardiogram measurements, and to be compact so as to be easily carried. The required apparatus for convenient personal use should be able to transmit data via wireless communication to a smartphone. To this end, the required apparatus should be battery-powered. To increase battery life while obtaining a compact size of the apparatus, the required apparatus should not include a display, and the electrocardiogram should be displayed on a smartphone.

In the present invention, in order to provide accurate and abundant ECG measurements, two limb leads are directly measured at the same time. As described later, in the present invention, four leads can be calculated and provided based on the two limb lead measurements performed simultaneously. Conventionally, regarding an electrocardiogram, "channel" and "lead" are used interchangeably to mean one ECG signal or ECG voltage. Regarding an electrocardiogram, the word "simultaneously" should be used very carefully. The phrase "simultaneously" means that operations are not "sequential". In other words, measuring two leads simultaneously should literally mean measuring two ECG voltages substantially at one moment. Specifically, when lead II is sampled while the voltage of lead I is sampled with a constant sampling period, measurements can be said to be performed simultaneously only if sampling lead II is performed within a shorter time than the sampling period from each time of sampling Lead I. The word "measurement" should also be used carefully. The word "measurement" should be mentioned only when a physical quantity is actually measured. In digital measurement, one measurement should mean one AD conversion. As will be described later, for example, by measuring lead I and lead III in electrocardiogram measurement, lead II can be calculated according to Kirchhoff's voltage law. In this case, lead II must be expressed as "calculated," not "measured," which can cause confusion.

One of the most difficult challenges in electrocardiogram measurement is to remove power line interference included in the electrocardiogram signal. A well-known method for removing power line interference is Driven Right Leg (DRL). Substantially, almost all electrocardiograms remove power line interference by the DRL. A drawback of the DRL is that one DRL electrode should be attached to the right leg or a lower right part of a torso. Therefore, in order to measure two limb leads using the DRL technique, conventional technology requires four electrodes including the DRL electrode to be brought into contact with the body. However, an important issue raised at this time is that a cable must be used or the size of the apparatus is increased because the DRL electrode should be brought into contact with the lower right abdomen. In other words, it is difficult to scale down an electrocardiogram measurement apparatus configured to measure two leads using a DRL electrode to the size of a credit card. Another important issue is that if the DRL electrode is arranged adjacent to another electrode and brought into contact with the human body, the voltage of the adjacent electrode is distorted because the voltage of the DRL electrode includes components of an electrocardiogram signal. Removing power line interference without using the DRL electrode is very difficult and requires use of a special circuit (In-Duk Hwang and John G. Webster, Direct Interference Cancelling for Two-Electrode Biopotential Amplifier, IEEE Transaction on Biomedical Engineering, Vol. 55, No. 11, pp. 2620-2627, 2008). In order to remove the power line interference, multiple filters having a significantly high quality factor (Q) may be required, and manufacturing and calibration of the multiple filters may be difficult.

The electrode impedance of a dry electrode is large, and accordingly the dry electrode generates greater power line interference. However, in the electrocardiogram measurement, for user convenience, it is necessary to use a dry electrode attached to the case surface of an electrocardiogram measurement apparatus without using a wet electrode connected to a cable. In addition, it is necessary to reduce the number of dry electrodes for user convenience. It is also required not to bring the DRL electrode into contact with the right leg or a lower right part of a torso. However, in the conventional technology, it is difficult to provide an electrocardiogram measurement apparatus that removes power line interference with a minimum number of electrodes and does not use a cable.

In order to solve the above problems and necessities, the present invention uses dry electrodes and does not use a cable for user convenience. To measure two limb leads simultaneously, the present invention uses two amplifiers, one electrode driver, and three electrodes connected thereto. The electrocardiogram apparatus according to the present invention provides a plate-shaped electrocardiogram apparatus having two dry electrodes separated from each other on one surface and one dry electrode on the other surface for user convenience. In addition, the present invention provides a method for removing power line interference in order not to use a DRL electrode.

As will be described later, the present invention discloses an electrocardiogram measurement apparatus including three electrodes, wherein the power line interference current flows concentrated through one electrode connected to the electrode driver, and two amplifiers connected to the other two electrodes among the three electrodes each amplify one electrocardiogram signal to measure two electrocardiogram signals simultaneously. Here, one amplifier serves to amplify one signal. In an actual configuration, one amplifier may represent a set composed of multiple cascaded amplification stages or active filters.

As described below, the conventional technology has failed to provide a technical solution provided by the present invention.

Righter (U.S. Pat. No. 5,191,891, 1993) discloses a watch-type device equipped with three electrodes. This device obtains only one ECG signal.

Amluck (DE 201 19965, 2002) discloses an electrocardiogram apparatus provided with two electrodes on the top and one electrode on the bottom. This apparatus measures only one lead. In addition, unlike the present invention, Amluck has a display and input/output buttons.

Wei et al. (U.S. Pat. No. 6,721,591, 2004) discloses that six electrodes including the ground electrode and RL electrode are used. Wei et al. discloses a method of measuring 4 leads and calculating the remaining 8 leads.

Kazuhiro (JP2007195690, 2007) discloses an apparatus equipped with a display and four electrodes including a ground electrode.

Tso (US Pub. No. 2008/0114221, 2008) discloses a meter including three electrodes. However, according to Tso, two electrodes are touched simultaneously with one hand to measure one limb lead, for example, lead I. Since one lead is measured at a time in this way, three measurements need to be performed sequentially to obtain three limb leads. In addition, according to Tso, even an augmented limb lead, which does not need to be measured directly, is directly measured and a separate platform is used for this measurement.

Chan et al. (US Pub. No. 2010/0076331, 2010) disclose a watch including three electrodes. However, according to Cho et al., three leads are measured using three differential amplifiers. In addition, Chan et al. uses three filters connected to each of the amplifiers to reduce the noise in a signal.

Bojovic et al. (U.S. Pat. No. 7,647,093, 2010) discloses a method for calculating 12 lead signals by measuring three special (non-standard) leads. However, to measure three leads, consisting of one limb lead (lead I) and two special (non-standard) leads obtained from a chest, five electrodes including one ground electrode, on both sides of a plate-shaped apparatus, and three amplifiers are provided.

Saldivar (US Pub. No. 2011/0306859, 2011) discloses a cellular phone cradle. Saldivar discloses that three electrodes are provided on one side of the cradle. However, Saldivar uses a lead selector and one differential amplifier 68 connected to two of the three electrodes to measure one lead sequentially (see FIG. 4C and paragraph [0054]). That is, according to Saldivar, 3 leads are measured sequentially one at a time.

Berkner et al. (U.S. Pat. No. 8,903,477, 2014) relates to a method of calculating 12 lead signals through sequential measurements carried out by sequentially moving an apparatus using 3 or 4 electrodes disposed on both sides of a housing. However, Berkner et al. does not disclose the detailed structure and shape of the apparatus, including how each electrode is connected internally. Most importantly, Berkner employs one amplifier 316 and one filter module 304. When one amplifier 316 and one filter module 304 are used, for example, measuring two leads requires two measurements to be performed sequentially. Specifically, Berkner discloses " . . . so in a system comprising only 3 electrodes, the reference electrode is different and shifts for each. lead measurement. This may be done by designated software and/or hardware optionally comprising a switch." The above technique indicates that Berkner uses one amplifier 316 and one filter 304 to measure one lead at a time and performs multiple measurements sequentially. That is, the method of Berkner et al. has many disadvantages compared to the method of measuring two leads simultaneously using three electrodes and two amplifiers as presented in the present invention.

Amital (US Pub. No. 2014/0163349, 2014) discloses that a common mode cancellation signal is generated from three electrodes in an apparatus provided with four electrodes and a common mode signal is removed by coupling the common mode cancellation signal to the other electrode (see claim 1). This technique is a traditional DRL method well known before Amital.

Thomson et al. (US Pub. No. 2015/0018660, 2015) disclose a smartphone case with three electrodes attached. The smartphone case of Thomson has a hole in the front such that the smartphone screen can be seen. However, it fails to present a method for measuring two leads simultaneously using two amplifiers. In addition, since the apparatus of Thomson uses ultrasonic communication, a communication-related issue can be raised if the smartphone and the apparatus are separated by even a slight distance (about 1 foot). Further, if the user changes one's smartphone the user may not be allowed to use the existing Thomson's smartphone case.

Drake (US Pub. No. 2016/0135701, 2016) discloses that three electrodes are provided on one side of a mobile device to provide 6 leads. However, Drake discloses "comprises one or more amplifiers configured to amplify analog signals received from the three electrodes" (see paragraph [0025] and claim 4). Therefore, Drake is not clear about a key part of the invention: how many amplifiers are used and how the amplifiers are connected to the three electrodes. Further, Drake discloses "The ECG device 102 can include a signal processor 116, which can be configured to perform one or more signal processing operations on the signals received from the right arm electrode 108, from the left arm electrode 110, and from the left leg electrode 112" (see paragraph [0025]). Therefore, Drake receives three signals. Also, Drake is not clear about whether three signals are received simultaneously or sequentially. Drake also discloses "Various embodiments disclosed herein can relate to a handheld electrocardiographic device simultaneous acquisition of six leads." (see paragraph [0019]), where Drake uses the word "simultaneous" incorrectly, inappropriately and indefinitely. The structure of the device of Drake can be considered to be similar to that of the device of Thomson. In Drake, three electrodes are disposed on one side of the apparatus. Therefore, as with Thomson et al., it is difficult to bring three electrodes into contact with both hands and the body simultaneously.

The device of Saldivar (WO 2017/066040, 2017) uses a lead selection stage 250 to connect three electrodes to one amplifier 210. In addition, the device of Saldivar performs six measurements sequentially to obtain six leads. In other words, the device of Saldivar does not measure multiple leads simultaneously. The device of Saldivar also directly measures three augmented limb leads sequentially.

DISCLOSURE

Technical Problem

Therefore, the present invention has been made in view of the above problems, and it is an object of the present invention to provide an electrocardiogram apparatus having three electrodes and two amplifiers associated with two limb leads to measure the two limb leads simultaneously with one electrocardiogram apparatus. It is medically very important to measure two limb leads simultaneously. This is because it is more time consuming and inconvenient to measure two leads sequentially. More importantly, two limb leads measured at different times may not correlate with each other and may cause confusion in detailed arrhythmia discrimination. The electrocardiogram apparatus according to the present invention includes a plate-shaped electrocardiogram apparatus having two dry electrodes separated from each other on one surface and one dry electrode disposed on the other surface for user convenience. It is another object of the present invention to provide a method for removing power line interference in order not to use a DRL electrode. It is an object of the present invention to disclose a convenient electrocardiogram measurement method bringing two electrodes into contact with two hands and one electrode into the body and an electrocardiogram measurement apparatus having a structure proper thereto.

Technical Solution

The appearance, operation principle, configuration, and usage of the electrocardiogram apparatus according to the present invention for solving the above problems are as follows. The present invention solves the above problems through systematic and analytical circuit design and software production.

In accordance with one aspect of the present invention, provided is an electrocardiogram measurement apparatus comprising:

a first electrode and a second electrode configured to receive two electrocardiogram voltages of a body part in contact therewith, respectively;

two amplifiers configured to receive the two electrocardiogram voltages from the first electrode and the second electrode, respectively;

one electrode driver configured to output a driving voltage;

a third electrode configured to receive the output of the electrode driver and transmit the output of the electrode driver to the body part in contact therewith;

an AD converter connected to an output terminal of each of the two amplifiers to convert output signals of the two amplifiers into two digital signals;

a microcontroller configured to receive the two digital signals of the AD converter; and a communication means configured to transmit the two digital signals.

The microcontroller is supplied with battery power.

The microcontroller controls the AD converter and the communication means.

The two amplifiers each receive and amplify one electrocardiogram voltage simultaneously, and an output impedance of the electrode driver is less than an input impedance of each of the two amplifiers.

FIG. 1 shows an electrocardiogram measurement apparatus 100 according to the present invention. The electrocardiogram measurement apparatus 100 includes three electrodes 111, 112, and 113 on the surface thereof. Two electrodes 111 and 112 spaced apart from each other by a predetermined distance are installed on one surface of the electrocardiogram measurement apparatus 100, and one electrode 113 is installed on the other surface.

FIG. 2 illustrates a method for a user to measure an electrocardiogram in a 6-channel mode using the electrocardiogram measurement apparatus 100 according to the present invention. The user makes contact with the electrodes 111 and 112 provided on one surface of the electrocardiogram measurement apparatus 100 with both hands, and brings the electrode 113 provided on the other surface into contact with the left lower abdomen (or left leg) of the user. When the three electrodes are brought into contact with the user's body in this way, two limb leads can be measured, and four leads can be additionally calculated and obtained as described below. The measurement method of FIG. 2 is provided by the present invention to obtain a 6-channel electrocardiogram most conveniently. In addition, the present invention provides an apparatus most suitable for the measurement method of FIG. 2. The principle of the measurement method is as follows.

A traditional 12-lead ECG is disclosed in, for example, [ANSI/AAMI/IEC 60601-2-25:2011, Medical electrical equipment-part 2-25: Particular requirements for the basic safety and essential performance of electrocardiographs]. In the traditional 12-lead ECG, three limb leads are defined as follows: lead I=LA−RA; lead II=LL−RA; lead III=LL−LA. In these equations, RA, LA, and LL denote the voltages of the right arm, left arm, and left leg, or body parts close to these limbs, respectively. Conventionally, in order to remove power line interference, a right leg (DRL) electrode is used. From the relationships above, one limb lead can be obtained from the other two limb leads. For example, lead III=lead II−lead I. Three augmented limb leads are defined as follows: aVR=RA−(LA+LL)/2; aVL=LA−(RA+LL)/2; aVF=LL−(RA+LA)/2. Therefore, the three augmented limb leads can be obtained from two limb leads. For example, aVR=−(I+II)/2. Therefore, when two limb leads are measured, the remaining four leads can be calculated and obtained. Accordingly, the present invention discloses an apparatus for simultaneously measuring two leads using three electrodes and two amplifiers to provide six leads. Here, one amplifier means that one signal is amplified. In an actual configuration, one amplifier may be configured as a set of multiple cascaded amplification stages or active filters. A standard 12-lead electrocardiogram consist of the six leads and six precordial leads from V1 to V6.

Modified chest leads (MCLS) are similar to the precordial leads and are medically very useful. In the principle of the present invention, the voltage of one electrode that is not connected to any amplifier among the three electrodes is substantially equal to the circuit common in the signal frequency band, as will be described later. Accordingly, the electrocardiogram measurement apparatus 100 according to the present invention is suitable for measuring one MCL among six MCLS from MCL1 to MCL6. This is because each MCL is a voltage at the position of the corresponding precordial lead referenced on the voltage of a body part to which the left hand is connected.

FIG. 3 illustrates a method for a user to measure MCL1 using the electrocardiogram apparatus according to the present invention in an MCL mode. For example, in order to measure MCL1 using the electrocardiogram apparatus according to the present invention, the user contacts the electrodes 111 and 112 provided on one surface of the electrocardiogram measurement apparatus 100 with both hands and brings the electrode 113 provided on the other surface into contact with the MCL position (for example, the V1 position in measuring MCL1), as shown in FIG. 3. In the present invention, in order for the user to measure MCLn, the user needs to bring the electrode 113 into contact with the MCLn position, that is, the Vn position on the user's body.

Hereinafter, an embodiment of the electrocardiogram measurement apparatus according to the present invention will be described with reference to FIGS. 4 and 5. FIG. 4 shows an electrical equivalent circuit model for explaining principles and embodiments of removing power line interference by the electrocardiogram measurement apparatus according to the present invention. FIG. 5 shows an electrical equivalent circuit model of an embodiment in which the electrocardiogram measurement apparatus according to the present invention simultaneously measures two channels of an electrocardiogram using two single-ended input amplifiers and one electrode driver.

In FIG. 4, a current source 450 is used to model power line interference. In addition, in FIG. 4, a human body is denoted by 430 and modeled by three electrode resistors 431, 432, and 433 connected to each other at one point. In FIG. 5, one electrocardiogram signal is modeled as one voltage source (461 or 462) existing between two electrode resistors. Since three electrodes are used in the present invention, in FIG. 5, it is modelled such that there are two ECG voltage sources 461 and 462 on the human body. This is because though there are three electrocardiogram voltages on the three electrodes (because the number of cases of selecting two of the three electrodes is 3), but only two electrocardiogram voltages are independent. The modeling for power line interference in FIG. 4 and the electrocardiogram signal in FIG. 5 is in a simplified form. However, the above models are suitable to clarify issues to be addressed. In addition, the above models clearly suggest what should be devised in the present invention. In addition, the present invention can be easily understood from the above models. The present invention has been devised based on the above models. Since the conventional arts do not use the above models, the conventional arts fail to accurately present a solution to the issues.

The present invention can be presented in various embodiments, as will be described later. However, the various embodiments of the present invention are commonly based on the following principle of the present invention. The principle of the present invention is devised for the present invention. The present invention differs from the conventional arts in that it does not use a DRL electrode compared to the DRL method used in the conventional arts.

A challenge that has not been overcome by a conventional electrocardiogram measurement apparatus that does not use a DRL electrode and is required to be overcome is to remove or reduce power line interference. Power line interference in the electrocardiogram measurement apparatus is caused by a current source having a substantially infinite output impedance due to a significantly high output impedance as shown in FIG. 4 (in FIG. 4, the power line interference current source is indicated by 450.). Accordingly, in order to remove the power line interference, it is necessary to minimize the impedance looking into the human body from the power line interference current source. The impedance looking into the human body from the power line interference current source is the sum of the impedance of the human body and the impedance of the electrocardiogram measurement apparatus. As a result, it is necessary to minimize the impedance of the electrocardiogram measurement apparatus looking into through the three electrodes. There exists an impedance called an electrode impedance or electrode resistance between each electrode used to measure the electrocardiogram and the human body (431, 432, and 433 in FIG. 4). Accordingly, in order to minimize the effect of the electrode impedance when measuring an electrocardiogram voltage, the electrocardiogram measurement apparatus should have a high impedance. Accordingly, the electrocardiogram measurement apparatus should satisfy two opposing conditions that a low impedance should be provided to remove power line interference and a high impedance should be provided to measure an electrocardiogram voltage.

A method that can be considered to satisfy the two opposing conditions, for example, when three electrodes are used, is to connect three large resistors to the three electrodes, respectively, combine the opposite ends of the three resistors at one point, and provide negative feedback of the common mode signals of the three electrodes to the one point at which the three resistors are combined. However, this method is practically difficult to use. This is because the impedance of the power line interference current source is large and thus the magnitude of the power line interference current will not decrease. Accordingly, in this case, the power line interference voltage induced in the three resistors is still quite large or the amplifiers may be saturated. In addition, since the magnitude of the power line interference current is not reduced and the impedances of the respective electrodes may be different, a different power line interference voltage is induced at a high level in each electrode. Accordingly, even if a differential amplifier is used, it is difficult to remove the power line interference induced in each electrode. This is the difficulty of the conventional arts.

Therefore, in the present invention, the power line interference current is concentrated and flows through only one of the electrodes installed in the electrocardiogram measurement apparatus. To this end, while three electrodes are connected to the human body, the impedance that the power line interference current source looks into the electrocardiogram measurement apparatus through the one electrode is minimizes. Thereby, the power line interference voltage (indicated by 440 $v_{body}$ in FIG. 4) induced in the human body by the power line interference current source is minimized. Since the power line interference voltage induced in the human body is minimized, the input impedances seen through the other electrodes of the electrocardiogram measurement apparatus may be increased, and the electrocardiogram voltage may be accurately measured. At this point, what is important is that the one electrode through which the power line interference current flows should not be used for measurement because a high power line interference voltage is induced at the one electrode. Accordingly, in the present invention, when three electrodes are used, two electrodes and two amplifiers to receive electrocardiogram signals from the two electrodes are used for measurement. In particular, it should be noted that two differential amplifiers cannot be used in the electrocardiogram measurement apparatus employing three electrodes because only two electrodes should be used for measurement. It should also be noted that, when negative feedback is used, if negative feedback is provided in all frequency bands then the electrocardiogram signals appear at the electrode and mixed with the power line interference voltage, and therefore negative feedback should be provided only at the power line interference frequency. Hereinafter, the present invention will be described in detail with reference to the drawings.

FIG. 4 and the subsequent drawings show only a part of the electrocardiogram measurement apparatus 100 according to the present invention for simplicity. In FIG. 4, the electrocardiogram measurement apparatus 100 according to the present invention comprises three electrodes 111, 112, and 113, two amplifiers 411 and 412, and one electrode driver (specifically, a band pass filter) 413. In FIGS. 4 and 5, the two amplifiers 411 and 412 employed in the present invention are not differential amplifiers, but are single-ended input amplifiers.

An important feature of the embodiment of the present invention shown in FIG. 4 is that the electrocardiogram measurement apparatus 100 comprises an electrode driver 413 represented as a band pass filter. That is, in FIG. 4 and the like, the electrode driver 413 may have a frequency characteristic of band pass. Accordingly, in the present invention, the electrode driver 413 may be described as a band pass filter. The input of the electrode driver 413 is connected to one electrode 112. The output of the electrode driver 413 drives the electrode 113 through the resistor 423 (it is fed back to the electrode 113). The resonance frequency or peak frequency of the electrode driver, that is, the band pass filter 413, is the same as the frequency of power line interference. In addition, the band pass filter 413 has a large Q. In FIG. 4, the input impedance of the band pass filter 413 is considerably large and the output impedance thereof is considerably small. The element value of the resistor 423 is represented by $R_o$. In the present invention, for simplicity, the resistor 423 is regarded as the output impedance of the electrode driver 413.

In the present invention, two of the three electrodes are connected to the circuit common of the analog circuit with the resistors 421 and 422, which have values $R_i$. The resistors 421 and 422 are regarded as input impedances of the amplifiers 411 and 412.

In FIG. 4, 430 is a model of a human body. There is a contact resistance, commonly called electrode impedance, between the human body and an electrode. In FIG. 4, the electrode impedances (electrode resistances) present between the human body 430 and the three electrodes 111, 112, and 113 are represented by resistors 431, 432, and 433, respectively. The element values of the electrode resistors 431, 432, and 433 are indicated by $R_{e1}$, $R_{e2}$, and $R_{e3}$, respectively.

In FIG. 4, 450 is a power line interference current source for modeling power line interference. Current $i_n$ of the power line interference current source 450 flows to the circuit common of the electrocardiogram apparatus 100 according to the present invention through the human body 430 and the three electrodes 111, 112, and 113. When the power line interference currents flowing through the three electrodes 111, 112, and 113 are represented by $i_{n1}$, $i_{n2}$, and $i_{n3}$, the following equation is established according to Kirchhoff's current law.

Equation 1

$$i_n = i_{n1} + i_{n2} + i_{n3} \qquad (1)$$

For circuit analysis, power line interference induced in the human body 430 is denoted by $v_{body}$. In FIG. 4, $v_{n1}$, $v_{n2}$, and $v_{n3}$ represent power line interference voltages at the electrodes 111, 112, and 113, respectively. In Equation 1, each current is given as follows.

Equation 2

$$i_{n1} = \frac{v_{body}}{R_i + R_{e1}} \qquad (2)$$

Equation 3

$$i_{n2} = \frac{v_{body}}{R_i + R_{e2}} \qquad (3)$$

Equation 4

$$i_{n3} = \frac{v_{body} + v_{n2} H(f)}{R_o + R_{e3}} \qquad (4)$$

Here,

Equation 5

$$v_{n2} = \frac{R_i}{R_i + R_{e2}} v_{body} \qquad (5)$$

Here, the transfer function of the band pass filter 413 is denoted by $-H(f)$. Using the equations above, the following equation is obtained.

Equation 6

$$i_n = \frac{v_{body}}{R_i + R_{e1}} + \frac{v_{body}}{R_i + R_{e2}} + \frac{v_{body}}{R_o + R_{e3}} \frac{R_i}{R_i + R_{e2}} H(f) + \frac{v_{body}}{R_o + R_{e3}} \qquad (6)$$

In the present invention, the element values of the circuit of FIG. 4 are used so that the following approximations are possible (Equations 7 and 8). Equations 7 and 8 are important components of the present invention.

Equation 7

$$R_i \gg R_{e1}, R_{e2}, \text{ or } R_{e3} \qquad (7)$$

Equation 8

$$R_i \gg R_o \qquad (8)$$

Then, the following approximation is established.

Equation 9
$$i_n \approx \frac{v_b}{R_o + R_{e3}}(1 + H(f)) \qquad (9)$$

The following equation is obtained from Equation 9.

Equation 10
$$v_{body} \approx (R_o + R_{e3})\frac{i_n}{1 + H(f)} \qquad (10)$$

In Equation 10, if there is no feedback, that is, H(f)=0, the following equation is established.

Equation 11
$$v_{body} \approx (R_o + R_{e3})i_n \text{ if } H(f)=0. \qquad (11)$$

By comparing Equation 10 and Equation 11, it can be seen that the present invention reduces the influence of power line interference current $i_n$ to the amount of feedback, or (1+H(f)). Therefore, if the magnitude of the gain at the resonance frequency of the band pass filter satisfies $|H(f_0)| \gg 1$, $v_{body} \approx 0$. Thus, the principle of removing power line interference in the present invention has been proved.

Using Equations 2 and 10, the following can be confirmed.

Equation 12
$$v_{n1} \approx \frac{R_i}{R_i + R_{e1}}(R_o + R_{e3})\frac{i_n}{1 + H(f)}$$
$$\approx (R_o + R_{e3})\frac{i_n}{1 + H(f)}$$
$$\approx v_{body} \qquad (12)$$

Now the following result is obtained for $v_{n3}$. From the above results, $v_{body} \approx 0$ and $i_{n3} \approx i_n$ can be used.

Equation 13
$$v_{n3} \approx v_{body} - i_{n3}R_{e3} \approx -i_n R_{e3} \qquad (13)$$

The following can be derived from Equations 12 and 13.

Equation 14
$$|v_{n3}| \gg |v_{n1}| \qquad (14)$$

This means that, if |H(f)| is large, as a result of feedback, almost all power line interference current flows through the electrode (the electrode 113 in FIG. 4) to which feedback is provided, and therefore the electrode to which feedback is provided is contaminated by power line interference while the electrodes (the electrodes 111 and 112 in FIG. 4) to which feedback is not provided are hardly influenced by power line interference. This in turn means that only the electrodes to which feedback is not provided should be used for electrocardiogram measurement and the electrode to which feedback is provided should not be used for the measurement. Accordingly, the effect of power line interference cannot be eliminated using a differential amplifier whose input is connected to the electrodes 111 and 113 or a differential amplifier whose input is connected to the electrodes 112 and 113. This is one of the important issues of the conventional arts.

Hereinafter, description will be given of the principle of obtaining two electrocardiogram channel signals using three electrodes according to the present invention. FIG. 5 shows an electrical equivalent circuit given when an electrocardiogram is measured using the electrocardiogram apparatus according to the present invention.

In FIG. 5, $v_1$, $v_2$, and $v_3$ represent the electrocardiogram signal voltages of the electrodes 111, 112, and 113, respectively. Voltage $v_2$ of the electrode 112 obtained by analyzing this equivalent circuit based on the principle of superposition is given as follows.

Equation 15
$$v_2 = -v_a \frac{(R_o + R_{e3})\|(R_i + R_{e2})}{(R_i + R_{e1}) + (R_i + R_{e3})\|(R_i + R_{e2})} \frac{R_i}{(R_i + R_{e2})} + $$
$$v_b \frac{(R_i + R_{e1})\|(R_i + R_{e2})}{(R_i + R_{e1})\|(R_o + R_{e2}) + (R_i + R_{e1})} \frac{R_i}{(R_i + R_{e2})} - $$
$$v_2 H(f) \frac{(R_i + R_{e1})\|(R_i + R_{e2})}{(R_o + R_{e3}) + (R_i + R_{e1})\|(R_i + R_{e2})} \frac{R_i}{(R_i + R_{e2})} \qquad (15)$$

In Equation 15, the symbol ∥ represents the value of parallel resistance. As in the previous equations, the conditions of Equations 7 and 8 can be assumed. In this case, voltage $v_2$ is approximated as follows.

Equation 16
$$v_2 \approx -v_a \frac{(R_o + R_{e3})}{(R_i + R_{e3})} \frac{R_i}{(R_i + R_{e2})} + v_b - v_2 H(f) \approx v_b - v_2 H(f) \qquad (16)$$

Accordingly, under the conditions of Equations 7 and 8, voltage $v_2$ is given as follows.

Equation 17
$$v_2 \approx v_b \frac{1}{1 + H(f)} \qquad (17)$$

From the above equation, it can be seen that if $|H(f_0)| \gg 1$, $v_2 \approx v_b$ in the signal band.

FIG. 6 shows a frequency response of the band pass filter used in the electrocardiogram measurement apparatus according to the present invention. In FIG. 6, the resonance frequency of the band pass filter is 60 Hz, the gain at the resonance frequency is 20, and Q=120. FIG. 7 shows that when the band pass filter of FIG. 6 is used, $v_b$ may be obtained with an accuracy of 98% at a frequency less than or equal to 40 Hz.

Similarly, voltage $v_1$ of the electrode 1 is obtained as follows.

Equation 18

$$v_1 = +v_a \frac{R_i}{(R_i + R_{e1}) + (R_o + R_{e3})\|(R_i + R_{e2})} + \\ v_b \frac{(R_i + R_{e1})\|(R_i + R_{e2})}{(R_o + R_{e3}) + (R_i + R_{e1})\|(R_i + R_{e2})(R_i + R_{e1})} - \\ v_2 H(f) \frac{(R_i + R_{e1})\|(R_i + R_{e2})}{(R_o + R_{e3}) + (R_i + R_{e1})\|(R_i + R_{e2})(R_i + R_{e1})} \quad (18)$$

When the conditions of Equations 7 and 8 are used, voltage $v_1$ is approximated as follows.

$$v_1 \approx +v_a + v_b - v_2 H(f) \approx v_a + v_2 \qquad \text{Equation 19}$$

The equation above is obtained using Equation 16. Equation 20 below is obtained from the equation above, and $v_a$ may be obtained by this equation. It can be seen from Equation 20 that $v_a$ can be obtained without the influence of the band pass filter.

Equation 20

$$v_1 - v_2 \approx +v_a \qquad (20)$$

Thus, the principle of obtaining signals of two electrocardiogram channels using two single-ended amplifiers according to the present invention has been described.

FIG. 8 shows an electrical equivalent circuit model for explaining the principle and embodiment of removing power line interference by the electrocardiogram measurement apparatus according to the present invention using common mode signal of two electrodes. Of course, even when the common mode signal is used, the power line interference current is concentrated and flows through an electrode 832 to which the output of an electrode driver 813 is fed back, and a power line interference voltage is present in the electrode 832. FIG. 9 shows an electrical equivalent circuit model of an embodiment of simultaneously measuring two channels of an electrocardiogram using one differential amplifier 811 and one single-ended input amplifier 812 while removing power line interference using the method of FIG. 8, that is, adopting common mode signal. As in the previous case where two single-ended input amplifiers are used, two electrocardiogram voltages may be obtained.

For simplicity, the circuit analysis of FIGS. 8 and 9 is omitted. In the embodiment of FIGS. 8 and 9, one electrode driver, that is, the band pass filter 813, applies a driving voltage to a human body part in contact with the electrode 112 through the output impedance $R_o$ and the electrode 112, as in the embodiment of FIGS. 4 and 5. That is, the electrode 112 is not connected to an amplifier for measuring the electrocardiogram voltage, but is connected to the electrode driver 813 through the output impedance 823. That is, the electrode 112 is not used in measuring the electrocardiogram voltage. When the peak value of the band pass filter is large, the transfer function H(f) of the band pass filter may be corrected or compensated for in order to realize $|H(f)| \gg 1$ in the signal band.

While one band pass filter 813 is used as one electrode driver in FIG. 8, one constant voltage source 1013 is used as one electrode driver in FIG. 10. The constant voltage source 1013 applies a driving voltage to a human body part in contact with the electrode 112 through a resistor 1023 having a small resistance $R_o$ and the electrode 112. Most of the power line interference current flows through the electrode 112. In order to further concentrate the power line interference current, the output impedance 1023 of the electrode driver 1013 may be reduced. This method is less effective in removing power line interference than the previous methods using a band pass filter. Even in the embodiment of FIG. 10, two electrocardiogram voltages are simultaneously amplified using two amplifiers connected to two electrodes except for the electrode in which power line interference current is concentrated. In the embodiment of FIG. 10, one differential amplifier 1011 and one single-ended input amplifier 1012 are used. The output of the single-ended input amplifier 1012 may include weak power line interference and a band pass filter 1033 may be used to further reduce power line interference.

In FIGS. 5, 9 and 10, it is important to drive one electrode using an electrode driver having a small output impedance in order to reduce the power line interference. The output of the electrode driver is transmitted, through the electrode, to a human body part that is in contact with the electrode. Once the power line noise is reduced, two single-ended input amplifiers may be used or one single-ended input amplifier and one differential amplifier to amplify the two electrocardiogram voltages received from the two electrodes.

The principle of the present invention is summarized as follows. The condition that the input impedance the power line interference current source looks into the electrocardiogram measurement apparatus should be low is satisfied by reducing the output impedance of the electrode driver connected to one electrode, and the condition that the input impedances the electrocardiogram signal voltages are looking into the electrocardiogram measurement apparatus should be high is satisfied by increasing the input impedances seen through the other two electrodes. Thereby, the electrocardiogram measurement apparatus according to the present invention may accurately measure the electrocardiogram signal voltage while reducing power line interference. Accordingly, the output impedance of the electrode driver of the electrocardiogram measurement apparatus according to the present invention is less than the input impedance of each of the two amplifiers.

Description has been given above regarding an embodiment in which power line interference is removed by applying the output of one electrode driver to one electrode, and two electrocardiogram voltages are measured simultaneously using two amplifiers of a large input impedance that receive two electrocardiogram voltages from two electrodes.

Advantageous Effects

The electrocardiogram measurement apparatus according to the present invention provides six electrocardiogram leads obtained simultaneously using the smallest number of electrodes (specifically, three electrodes). When the electrocardiogram measurement apparatus according to the present invention is used in the MCL mode, one limb lead (specifically, Lead I) and one MCL may be measured.

Since the portable electrocardiogram measurement apparatus according to the present invention has a size of one credit card, it is convenient to carry the apparatus, and multiple electrocardiograms may be obtained most conveniently regardless of time and place. In addition, since the electrocardiogram measurement apparatus according to the present invention is capable of wirelessly communicating with a smartphone, the electrocardiogram measurement apparatus may be conveniently used without substantial limitation on the distance between the electrocardiogram measurement apparatus and the smartphone.

In addition, when the electrocardiogram measurement apparatus according to the present invention is not in use, all circuits except the current detectors are turned off and only the microcontroller enters a sleep mode. When the electrocardiogram measurement apparatus is used, only necessary circuits are supplied with power, and the microcontroller enters an activation mode. Therefore, consumption of power of the battery embedded in the electrocardiogram measurement apparatus may be reduced to the maximum degree.

In addition, the electrocardiogram measurement apparatus according to the present invention does not include a mechanical power switch or a selection switch. Accordingly, the measurement apparatus may be designed to be compact and slim, and may not lead to unnecessary troublesome use of a switch by the user, failure and finite service life of the switch, or an increase in manufacturing cost.

Further, since the electrocardiogram measurement apparatus according to the present invention does not include a display such as an LCD, there may no possibility of failure and deterioration of the display, and the apparatus may not lead to an increase in manufacturing cost, and may be manufactured in a compact size and convenient to carry.

BEST MODE

Figure 1:
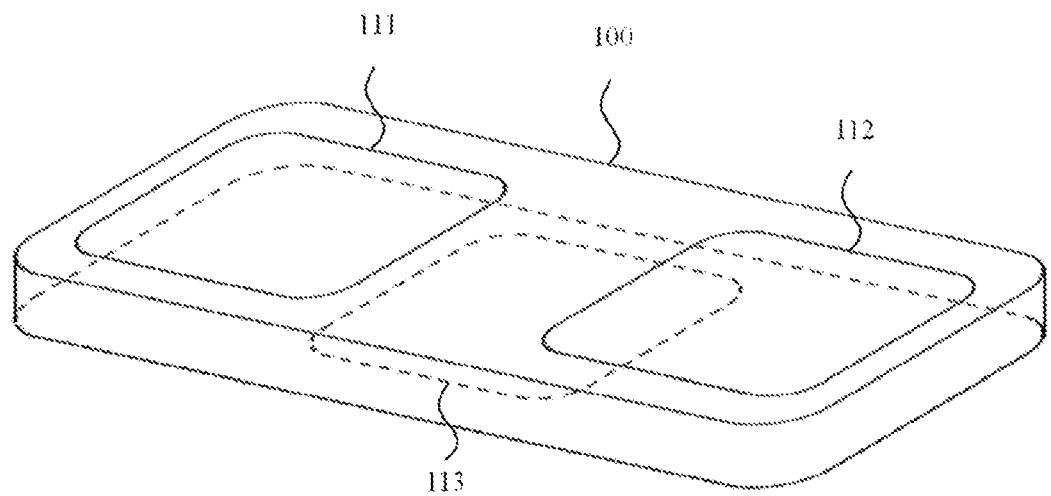
FIG. 1 is a perspective view of an electrocardiogram measurement apparatus having three electrodes according to the present invention.
Figure 2:
FIG. 2 illustrates a method for measuring an electrocardiogram in a 6-channel mode using the electrocardiogram measurement apparatus 100 according to the present invention.
Figure 3:
FIG. 3 illustrates a method for measuring an electrocardiogram in an MCL mode using the electrocardiogram apparatus according to the present invention.
Figure 4:
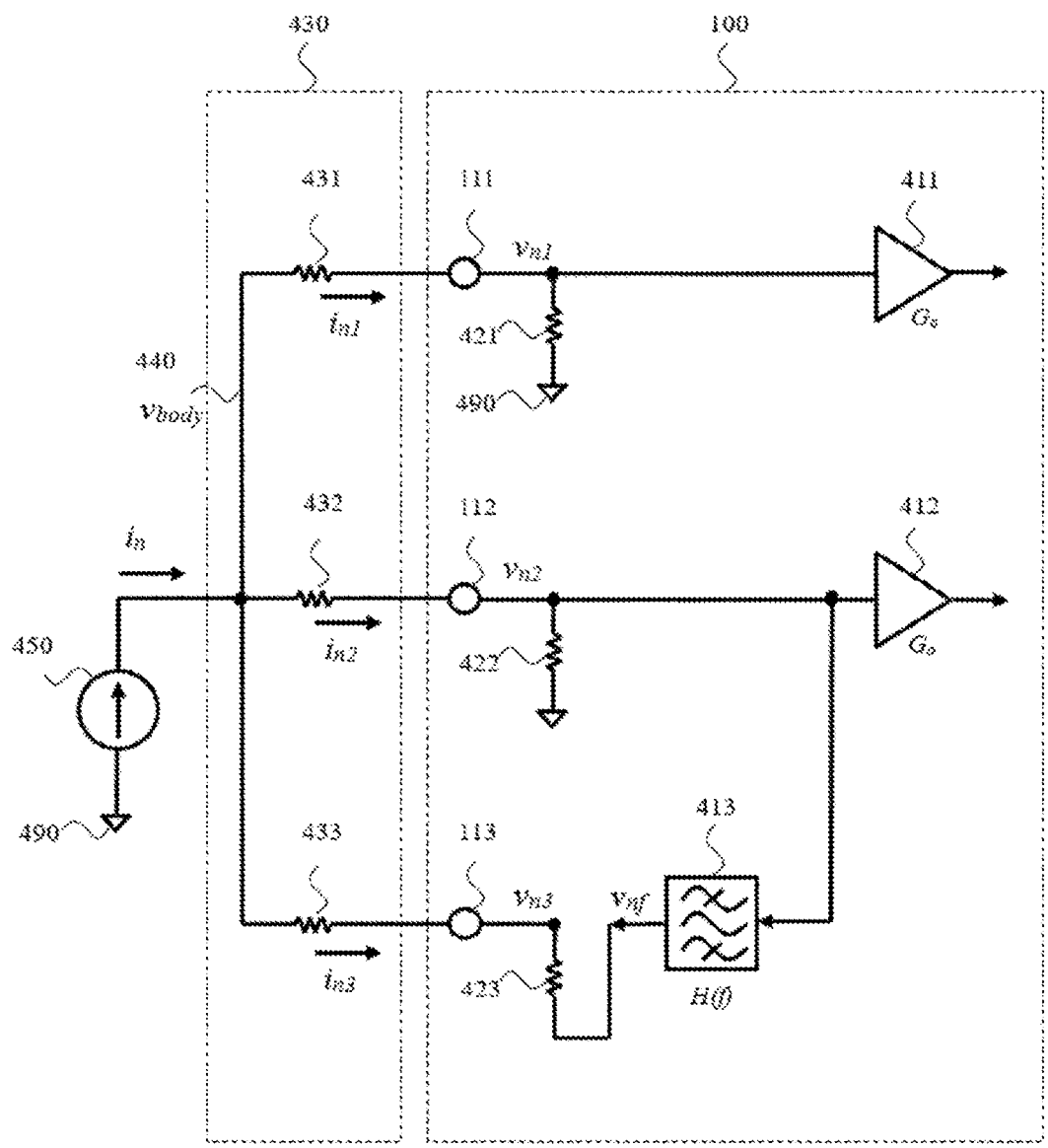
FIG. 4 shows an electrical equivalent circuit model for explaining the principle and embodiment of removing power line interference by the electrocardiogram measurement apparatus according to the present invention.
Figure 5:
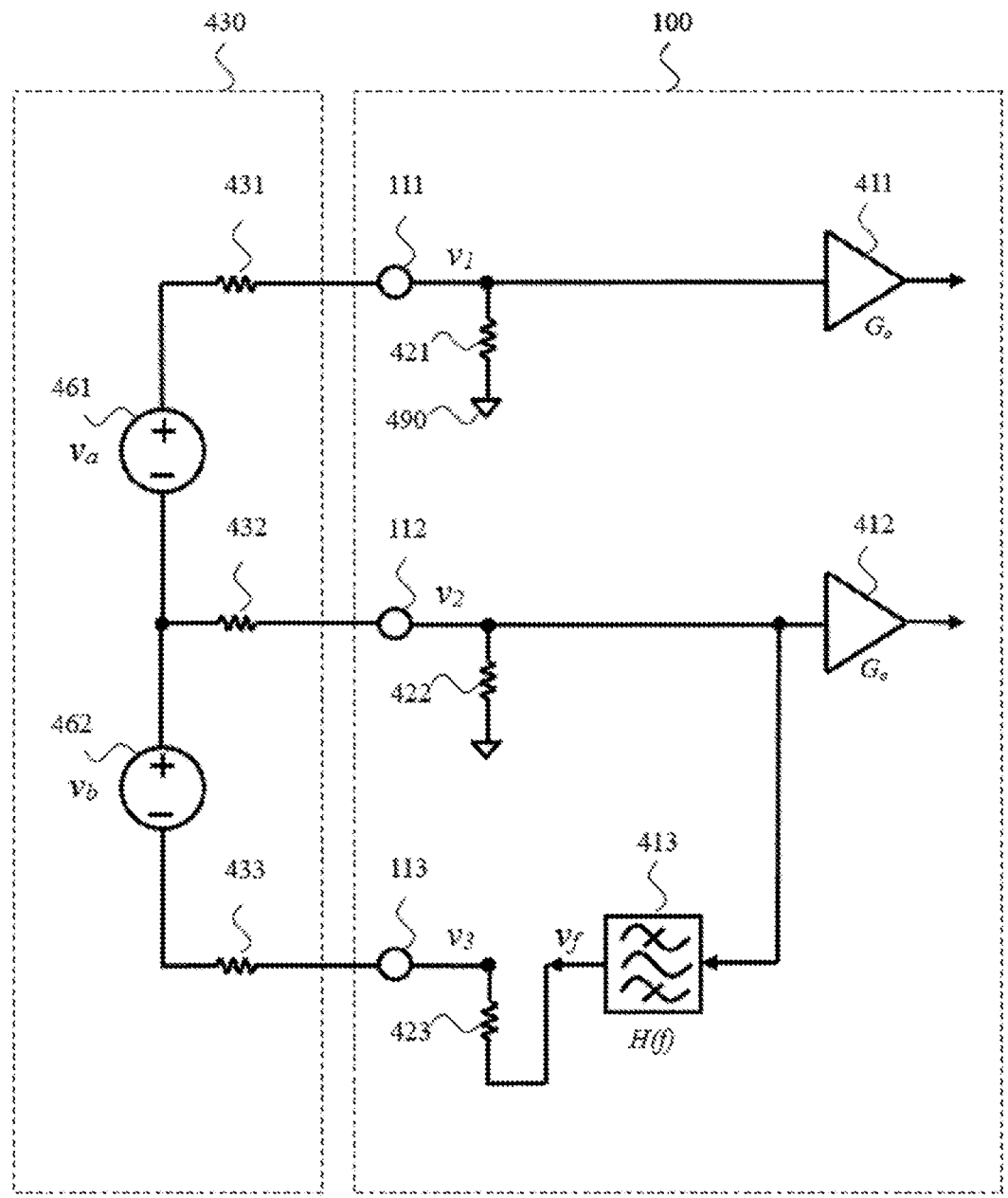
FIG. 5 shows an electrical equivalent circuit model of an embodiment in which the electrocardiogram measurement apparatus according to the present invention simultaneously measures two channels of an electrocardiogram using two single-ended input amplifiers and one band pass filter (electrode driver).
Figure 6:
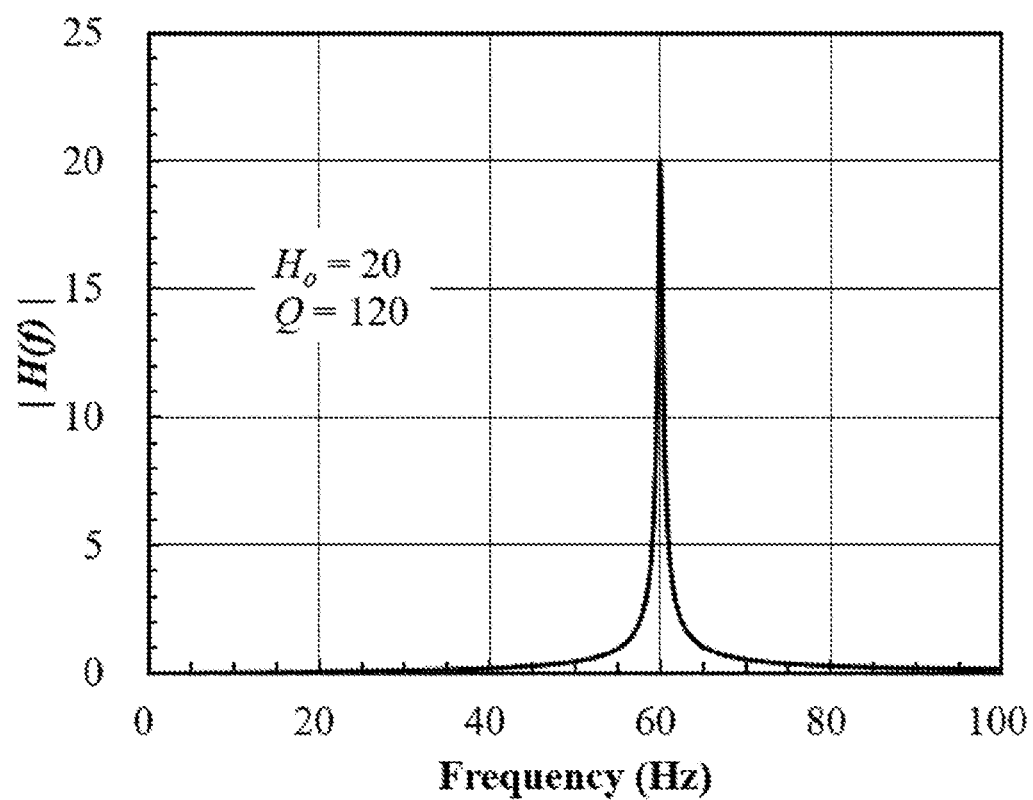
FIG. 6 shows a frequency response of the band pass filter used as an electrode driver in the electrocardiogram measurement apparatus according to the present invention.
Figure 7:
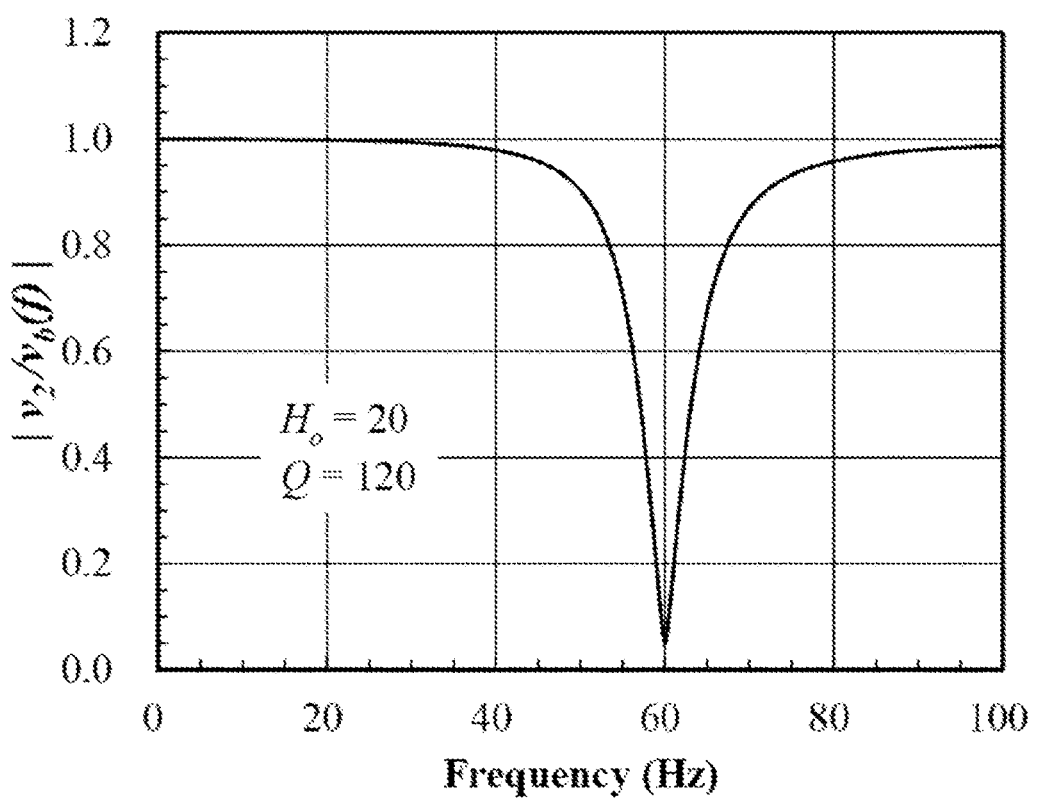
FIG. 7 shows a frequency response of one signal channel when a band pass filter is used as an electrode driver in the electrocardiogram measurement apparatus according to the present invention.
Figure 8:
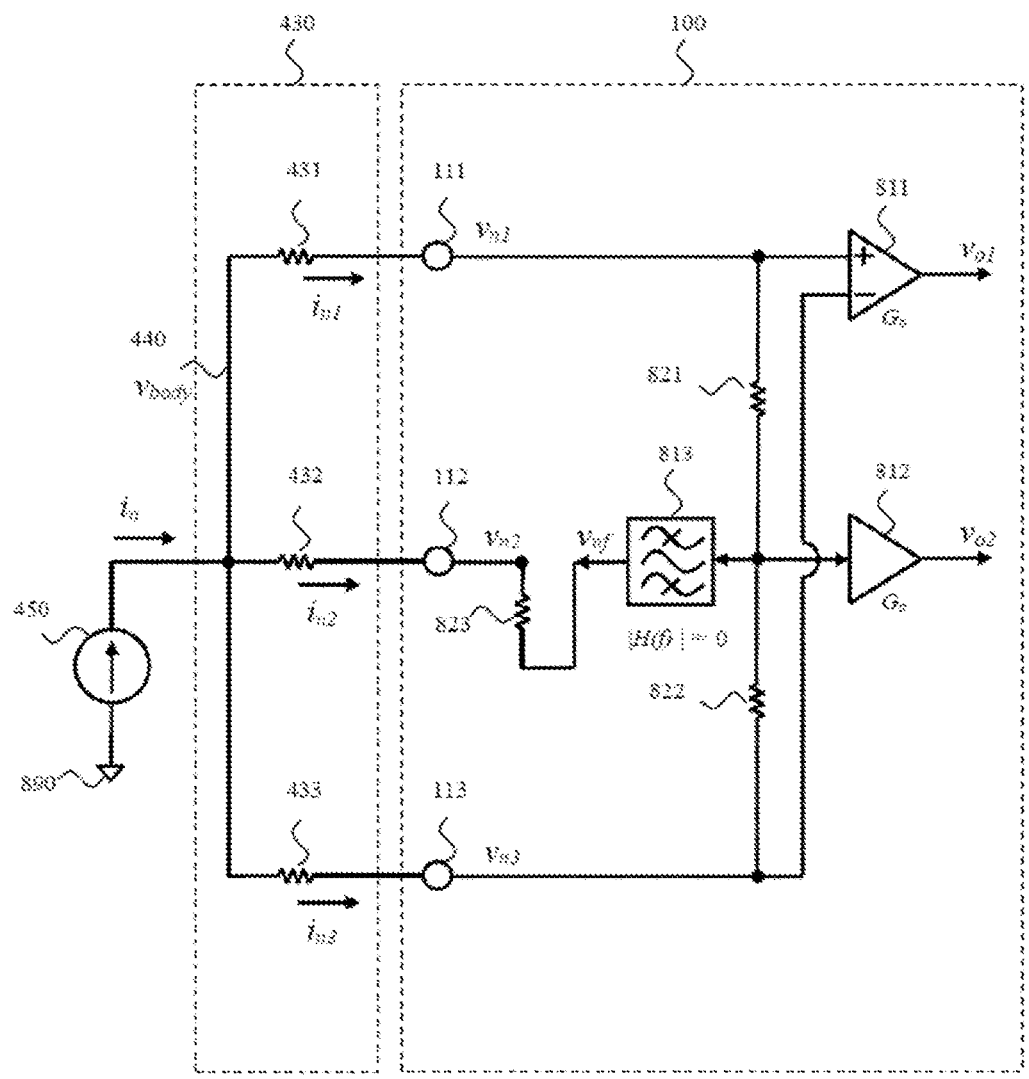
FIG. 8 shows an electrical equivalent circuit model for explaining the principle and embodiment of removing power line interference by the electrocardiogram measurement apparatus according to the present invention using the common mode signal.
Figure 9:
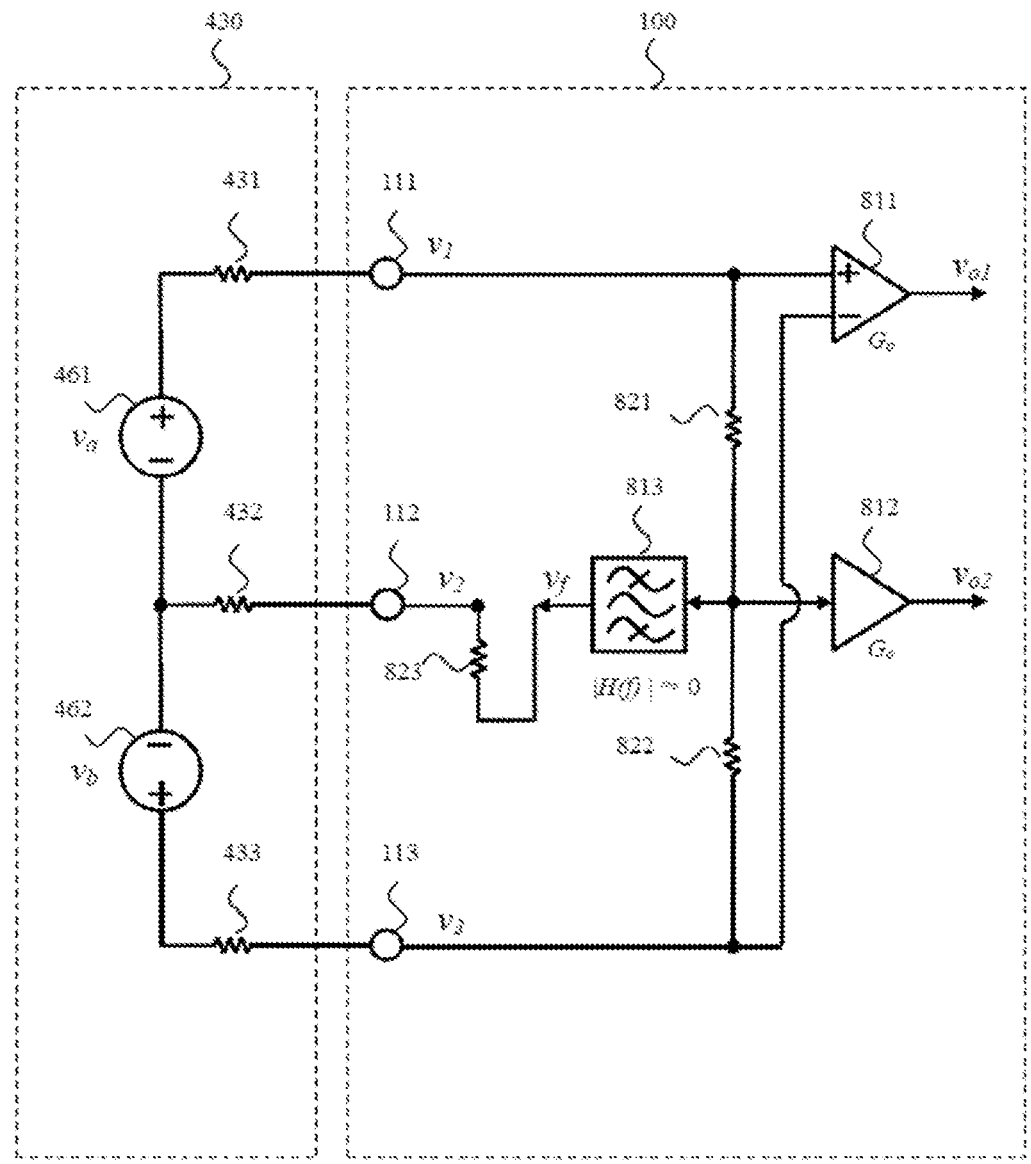
FIG. 9 shows an electrical equivalent circuit model of an embodiment of simultaneously measuring two channels of an electrocardiogram by the electrocardiogram measurement apparatus according to the present invention, using one differential amplifier, one single-ended input amplifier and one band pass filter (electrode driver) in removing power line interference using the common mode signal.
Figure 10:
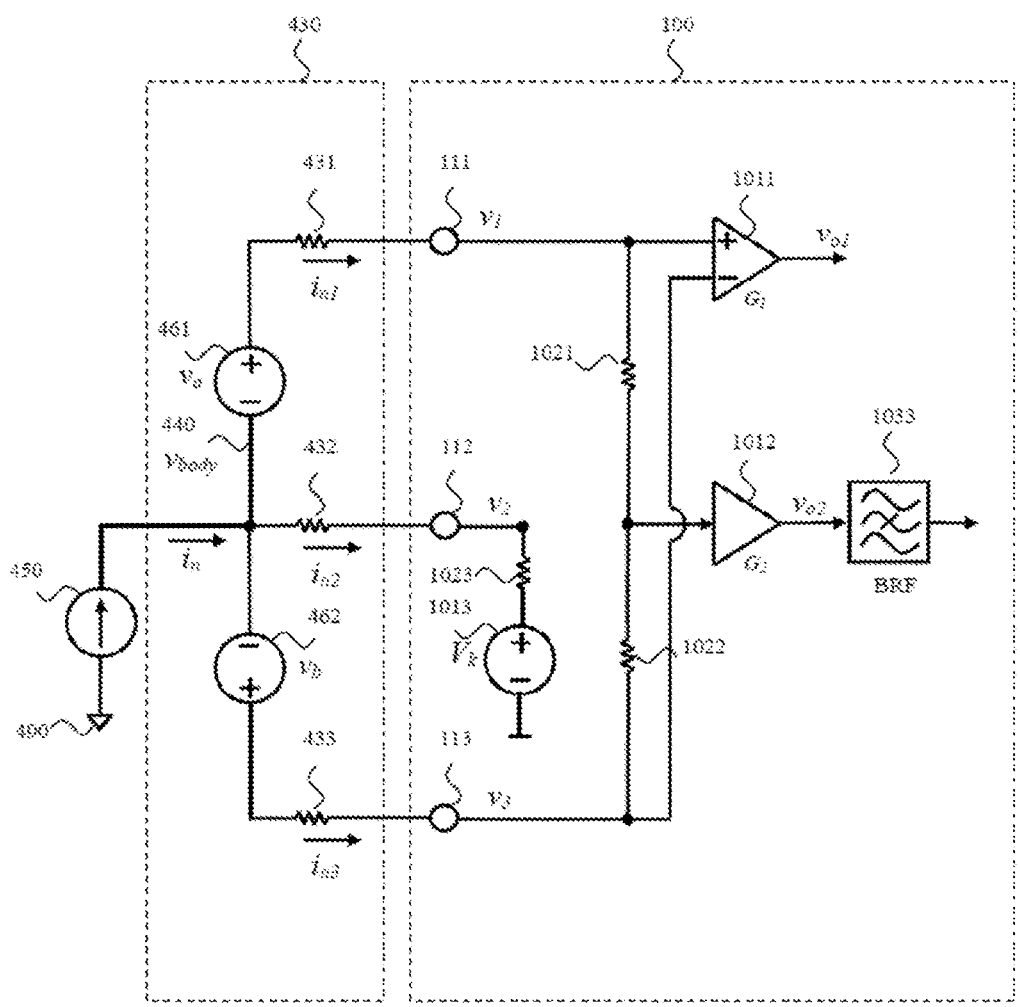
FIG. 10 is another embodiment of simultaneously measuring two channels of an electrocardiogram by the electrocardiogram measurement apparatus according to the present invention using one differential amplifier, one single-ended input amplifier, and one constant voltage generator (electrode driver).

Hereinafter, an embodiment according to the present invention will be described with reference to the drawings. In this embodiment, an electrocardiogram (ECG) measurement apparatus is described as including three electrodes, but is not limited thereto. The electrocardiogram measurement apparatus may include three or more electrodes. An important embodiment of the present invention has been described above based on FIGS. 4 to 10 to explain the principle of the present invention.

The portable electrocardiogram measurement apparatus according to the present invention may be in the form of a credit card and have a thickness of 6 mm or less in order to enhance portability. Since the portable electrocardiogram measurement apparatus according to the present invention is portable, it uses a battery. When a CR2032 type battery is employed, the service life thereof may be about 2 years.

In addition, to make the portable electrocardiogram measurement apparatus compact, either a mechanical power switch or a selection switch may not be provided. In addition, to reduce power consumption, a display is not employed.

The portable electrocardiogram measurement apparatus according to the present invention may employ a current detector in order not to use a mechanical power switch or a selection switch. The current detector is always supplied with power required for operation and waits to generate an output signal when an event occurs. When a user brings multiple electrodes into contact with the body to measure an electrocardiogram, a loop of minute current that can flow through the human body is generated. Accordingly, when the body is electrically connected to the current detector, the current detector causes the minute current to flow through the body. Upon detecting the minute current, the current detector generates an output signal. When the portable electrocardiogram apparatus is not in use, only the current detector operates, and the other circuits are powered off, and the microcontroller waits in a sleep mode in order to increase the battery usage time. At this time, when an event of touching two electrodes by both hands occurs and the current detector generates an output signal, the microcontroller is activated to power on the electrocardiogram circuit to perform electrocardiogram measurement. The current detected by the current detector is supplied from the battery provided in the portable electrocardiogram measurement apparatus, and is a direct current.

The electrocardiogram measurement apparatus 100 according to the present invention may further include a function of measuring blood properties such as blood glucose level, ketone level, or international normalized ratio (INR). Accordingly, in this embodiment, the electrocardiogram measurement apparatus 100 will be described as an example for measuring an electrocardiogram and blood properties together. The blood glucose level or ketone level may be measured using an amperometric technique. The INR is a measure of the tendency to coagulate blood and may be measured for capillary blood using an electric impedance technique, the amperometric technique, a mechanical technique, or the like. One blood test strip insert port through which a blood test strip required for the blood property test can be inserted may be provided in the case of the electrocardiogram measurement apparatus according to the present invention.

In an embodiment of the electrocardiogram measurement apparatus 100 according to the present invention, a thermometer function may be included. A suitable type to include the thermometer function in the electrocardiogram measurement apparatus 100 according to the present invention is a contact type, and a suitable temperature sensor is a thermistor. In order to measure body temperature using the electrocardiogram measurement apparatus 100 including the thermometer function according to the present invention, a user brings a portion of the electrocardiogram measurement apparatus 100 to which the temperature sensor is attached into contact with the user's forehead or armpit. To accurately measure the body temperature, the temperature of the skin should not be changed by the portion of the electrocardiogram measurement apparatus 100 to which the temperature sensor is attached.

Figure 11:
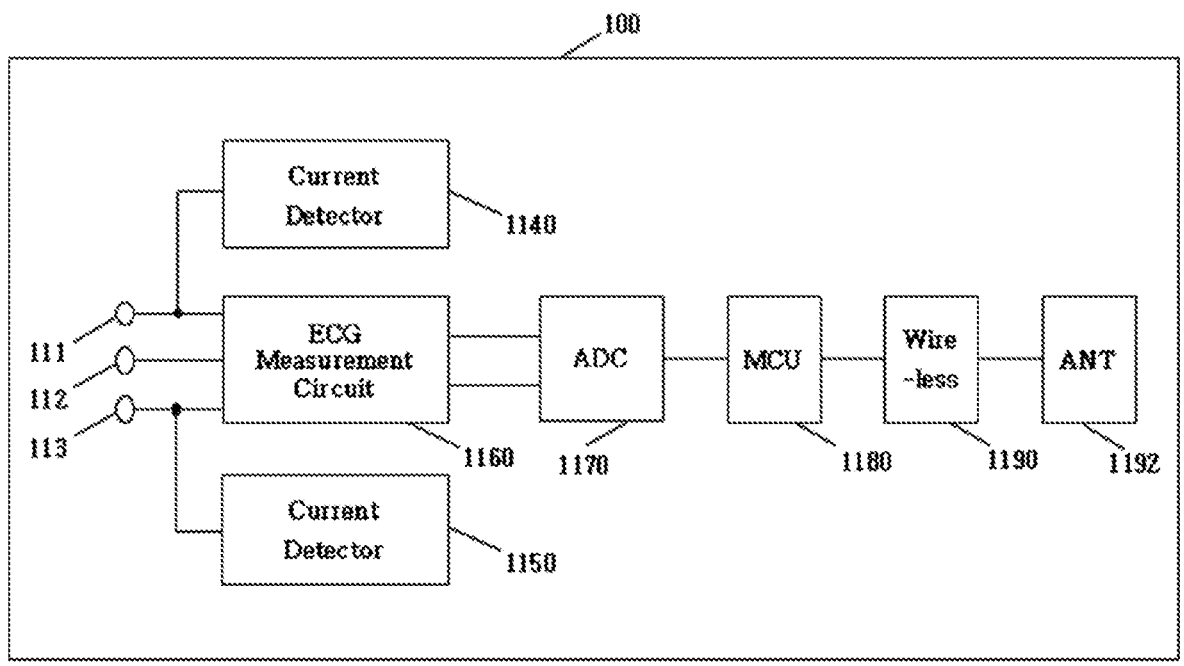
FIG. 11 is a block diagram of a circuit embedded in the electrocardiogram measurement apparatus according to the present invention.

FIG. 11 is a block diagram of a circuit embedded in the electrocardiogram measurement apparatus according to the present invention. Although not shown in FIG. 11 for clarity of the invention, the electrocardiogram measurement apparatus according to the present invention may include a blood test circuit and a blood test strip insert port. The function and operation of each block in FIG. 11 are described below. When the user touches a pair of electrodes 111 and 112 with both hands, an electrocardiogram current detector 1140 allows minute current to flow through both hands and detects the minute current flowing through both hands. Then, the current detector 1140 generates a signal to change the microcontroller 1180 from a sleep mode to an active mode. Then, the microcontroller 1180 powers on the electrocardiogram measurement circuit 1160 and the AD converter 1170. The electrocardiogram measuring circuit 1160 amplifies two electrocardiogram signals through two amplifiers and generates two outputs. The AD converter 1170 receives the two outputs of the electrocardiogram measurement circuit 1160, and the outputs of the AD converter 1170 are transmitted to the smartphone 210 through the wireless communication means 1190 and the antenna 1192. Upon receiving data, the smartphone 210 displays multiple electrocardiogram waveforms. After the measurement for a certain duration, the microcontroller 1180 enters the sleep mode and waits for the next touch of both hands.

When the electrocardiogram measurement apparatus according to the present invention is brought into contact with both hands and the lower left abdomen, six leads can be displayed at a time. However, when it is inconvenient to bring the electrocardiogram measurement apparatus into contact with the lower left abdomen or only one lead is to be measured, the electrocardiogram measurement apparatus may automatically determine whether the user intends to measure only one lead or six leads. When the user touches the electrocardiogram measurement apparatus with only both hands to measure only one lead, only one current detector 1140 detects current. Then, only Lead I is displayed on the smartphone. When the user touches the electrocardiogram measurement apparatus with both hands and the lower left abdomen to measure six leads, both the current detector 1140 and the current detector 1150 detect currents. The six leads are then displayed on the smartphone. Each of the blocks shown in FIG. 11 may be implemented based on conventional technology using commercialized parts.

Figure 12:
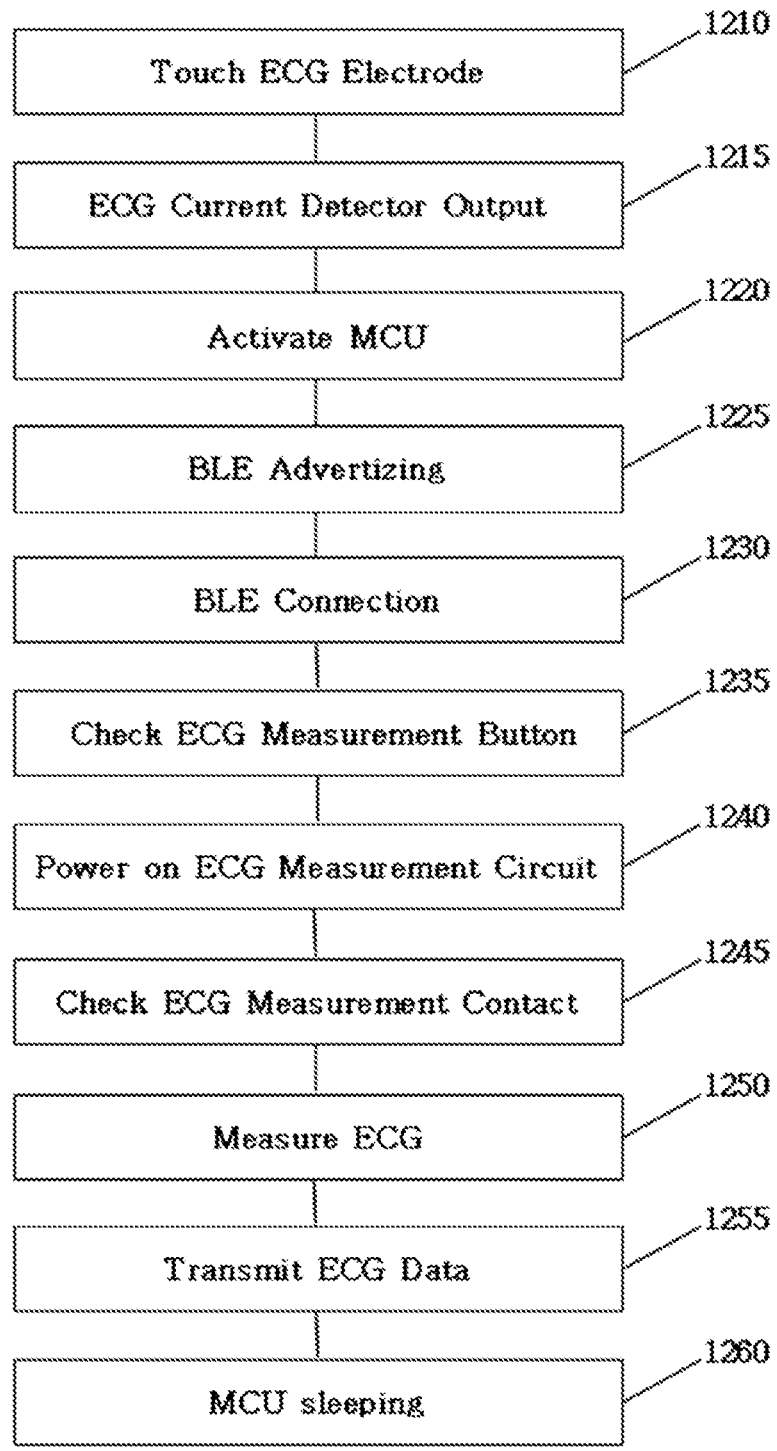
FIG. 12 is an operation flowchart of the electrocardiogram measurement apparatus according to the present invention.

FIG. 12 is an operation flowchart of the electrocardiogram measurement apparatus 100 according to the present invention in measuring an electrocardiogram. In order to measure the electrocardiogram, a user touches the pair of electrodes 111 and 112 of the electrocardiogram measurement apparatus 100 with both hands (1210). Then, the current detector detects minute current flowing through the human body between both hands and generates an output signal (1215). The output signal activates the microcontroller 1180 by generating an interrupt of the microcontroller 1180 (1220). The activated microcontroller 1180 activates the wireless communication means 1190. Hereinafter, a case where the wireless communication means 1190 is a Bluetooth low energy device will be described. The wireless communication means 1190 of the electrocardiogram measurement apparatus 100 advertises as a Bluetooth low energy peripheral (1225). At this time, the smartphone that is performing scanning as a Bluetooth low energy central device discovers the electrocardiogram measurement apparatus 100 and attempts to connect thereto. At this time, when the electrocardiogram measurement apparatus 100 approves the connection, the smartphone and the electrocardiogram measurement apparatus 100 are Bluetooth low energy connected (1230). At this time, the electrocardiogram measurement apparatus 100 may check whether the user has touched the electrocardiogram measurement button of the smartphone to actually measure an electrocardiogram (1235).

Once it is confirmed that electrocardiogram measurement is requested, the microcontroller 1180 powers on the electrocardiogram measurement circuit 1160 (1240). This operation may be performed by connecting an output pin of the microcontroller 1180 to the electrocardiogram measurement circuit 1160 and setting the voltage of the output pin to High. Next, it is checked whether the pair of electrodes 111 and 112 are in touch with both hands, using the current detector (1245). This step is to determine when the microcontroller 1180 should start ECG measurement, that is, AD conversion. That is, this step is to check whether both hands continuously remain in contact with the electrodes 111 and 112.

After the above steps, the microcontroller 1180 starts the ECG measurement (1250). That is, the microcontroller 1180 performs AD conversion according to a preset AD conversion cycle and brings an AD conversion result. In the present invention, two electrocardiogram signals are measured. The measured ECG data is transmitted to the smartphone 210 (1255). When a preset measurement time of, for example, 30 seconds, elapses, the microcontroller 1180 enters the sleep mode (1260).

All circuits of FIG. 11 are driven by a battery embedded in the electrocardiogram measurement apparatus 100. In the example of FIG. 11, any of a mechanical power switch, a mechanical selection switch, and a display may not be provided. In FIG. 11, when the electrocardiogram measurement apparatus 100 does not perform measurement, the electrocardiogram current detector and the microcontroller 1180 each consume approximately 1 uA, and all the other blocks are completely powered off.

Figure 13:
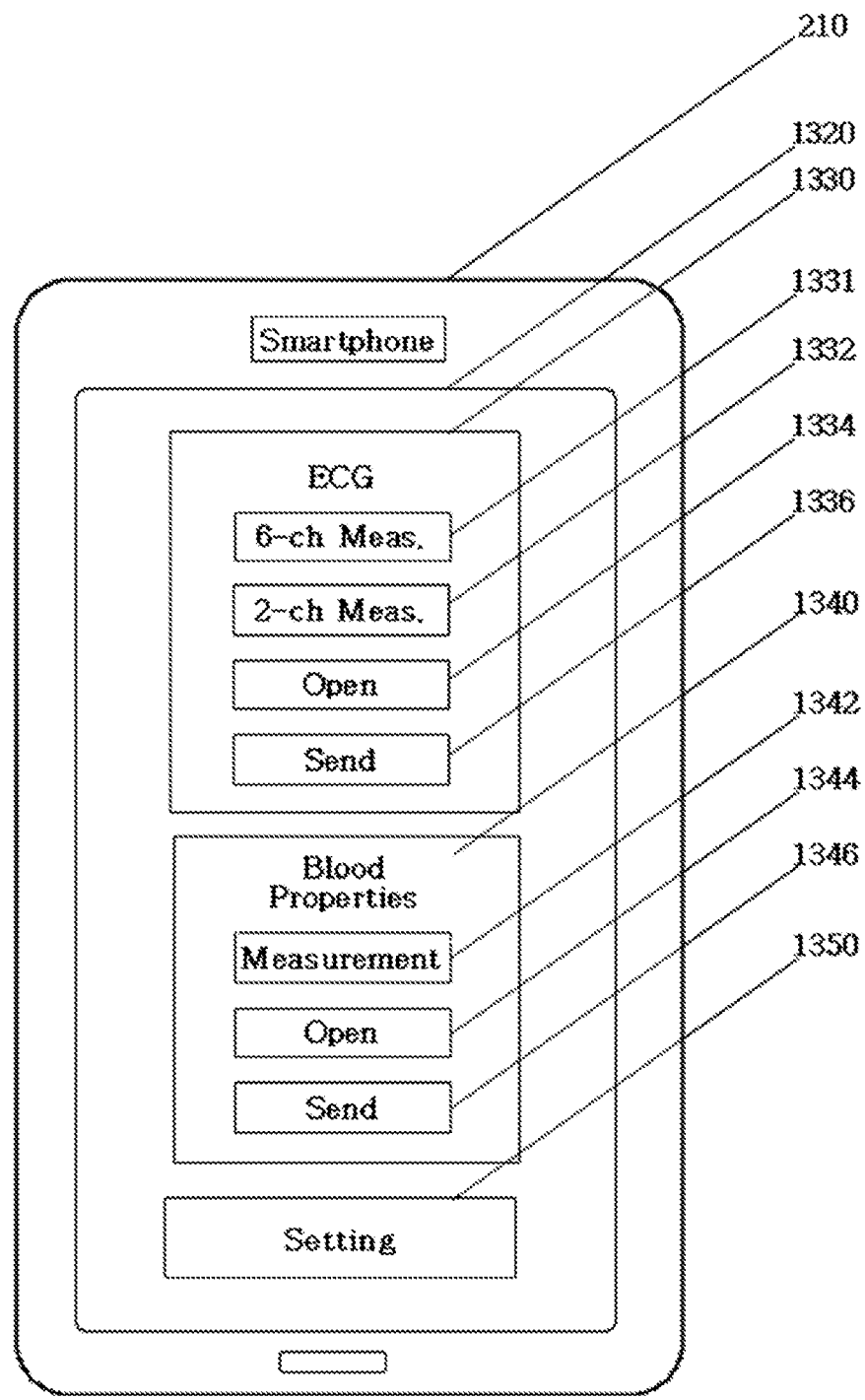
FIG. 13 shows an initial screen of a smartphone when a smartphone app is executed to use the electrocardiogram measurement apparatus according to the present invention

The electrocardiogram measurement apparatus 100 according to the present invention is used together with the smartphone 210. FIG. 13 shows an initial screen of a smartphone when a smartphone app according to the present invention is executed. When the smartphone app is executed, touch buttons 1331, 1332, 1334, 1336, 1342, 1344, 1346, and 1350 are displayed on the display 1320 of the smartphone 210. The buttons 1331, 1332, 1334, and 1336 related to the electrocardiogram are configured in an electrocardiogram box 1330. When the electrocardiogram measurement apparatus 100 according to the present invention includes a function of measuring blood properties, the buttons 1342, 1344 and 1346 related to blood properties are configured in a blood glucose box 1340. To measure an electrocardiogram, the user selects and touches one of the electrocardiogram measurement mode buttons 1331 and 1332 wanted. When the user is to measure the electrocardiogram in a 6-channel mode, the user touches the button 1331. When the user is to measure the electrocardiogram in an MCL mode, the user touches the button 1332. Then, when the user remains touching the pair of electrodes 111 and 112 of the electrocardiogram measurement apparatus 100 with both hands, the electrocardiogram measurement apparatus 100 measures the electrocardiogram as described above. The measured ECG data is displayed in the form of a chart on the smartphone display 1320 and is stored in the smartphone 210. The open button 1334 is touched to view, in a chart form, the ECG measurement data stored in the past. To send the stored data to a doctor or a hospital, the Send button 1336 is touched. The Setting button 1350 is touched when a user's name, date of birth, gender, address, etc. are to be recorded or when options are to be set.

Figure 14:
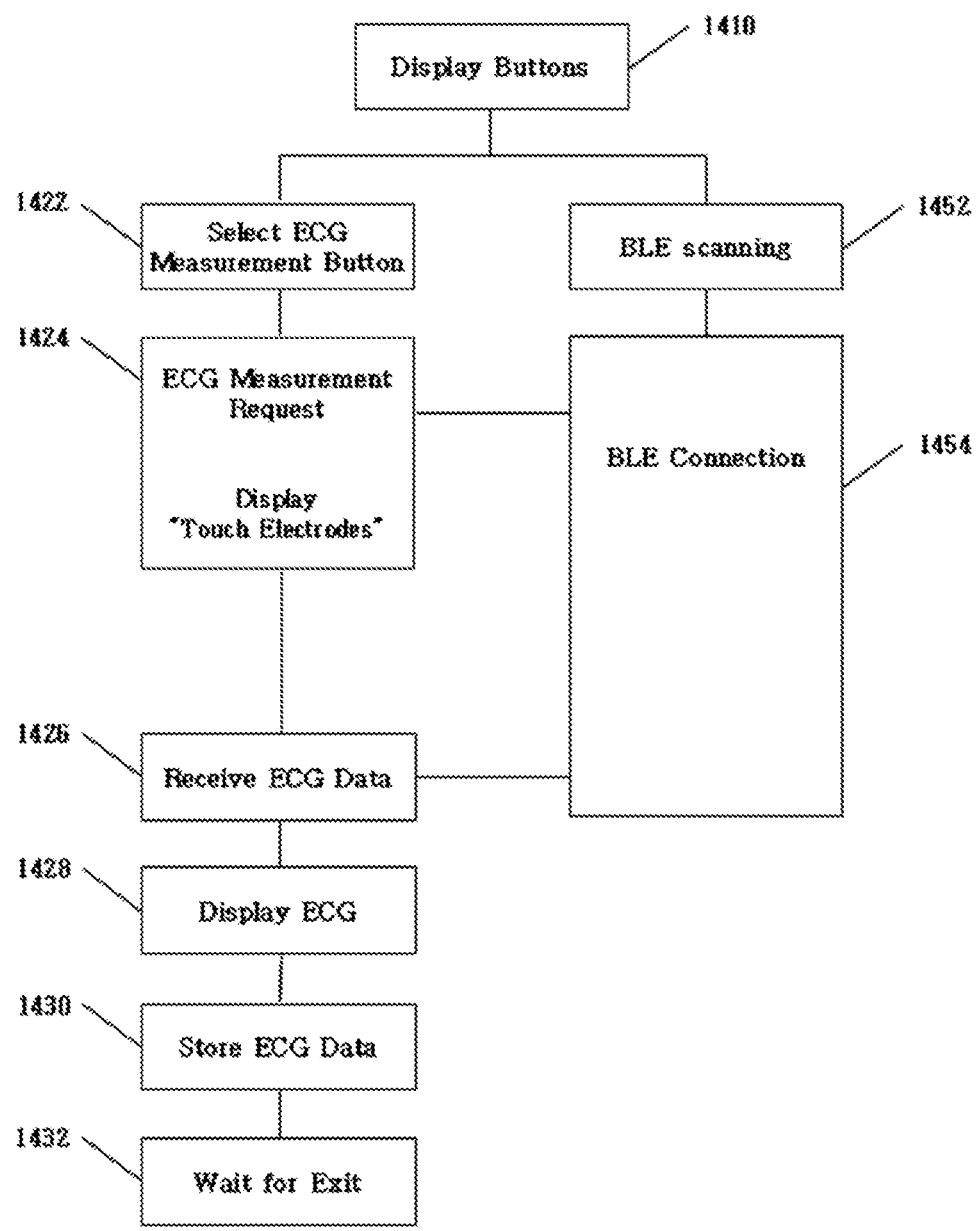
FIG. 14 is a flowchart illustrating a smartphone app operated when the electrocardiogram measurement apparatus according to the present invention is used.

FIG. 14 is a flowchart illustrating a smartphone app according to the present invention. For simplicity, only the process of measuring an electrocardiogram will be described. As shown in FIG. 14, the flow operated in measuring the electrocardiogram is composed of two branches: a central branch 1422, 1424, 1426, 1428, 1430, 1432, and a Bluetooth low energy (BLE) branch 1452, 1454. When the app starts, various buttons appear on the smartphone display 1320 (1410), and then the BLE branch 1452 1454 for performing Bluetooth low energy communication is started. The user who wants to measure the electrocardiogram touches one of the ECG measurement buttons 1331 and 1332 (1422).

When the user touches one of the ECG measurement buttons 1331 or 1332 (1422), an ECG measurement request signal is sent to the BLE branch 1452, 1454 (1424). In addition, a message instructing the user to contact electrodes according to the ECG measurement mode is displayed on the smartphone display 1320 (1424). In the BLE branch 1452, 1454, an ECG measurement request signal is sent to the electrocardiogram measurement apparatus 100 (1454).

The electrocardiogram measurement apparatus 100 receiving the ECG measurement request signal performs the electrocardiogram measurement task described in FIG. 12 and transmits measured ECG data to the BLE branch 1452, 1454. The BLE branch 1452, 1454 transfers the ECG data received from the electrocardiogram measurement apparatus 100 to the central branch 1422, 1424, 1426, 1428, 1430, 1432. Then, the central branch 1422, 1424, 1426, 1428, 1430, 1432 receives the ECG data (1426). The received ECG data is displayed in a chart form on the smartphone display 1320 in the central branch 1422, 1424, 1426, 1428, 1430, 1432 (1428). When all the ECG measurements are completed, the measured ECG data is stored in a file format in a smartphone storage device (1430). While the measured ECG data is being displayed in the form of a chart on the smartphone display 1320, the smartphone app waits for the user to end the app by pressing the app exit button (1432).

According to the present invention, the user may be provided with desired results without undergoing abnormality in the number of cases of all possible operation sequences by using the electrocardiogram measurement apparatus 100, which is not provided with a mechanical switch, a selection switch, or a display, and a smartphone app simplified to use.

The present invention has been described in detail regarding a case where an electrocardiogram is measured using the single portable electrocardiogram measurement apparatus 100 and a smartphone app, but the electrocardiogram measurement apparatus 100 according to the present invention is not limited thereto. Various measurement items may be additionally measured.

Figure 15:
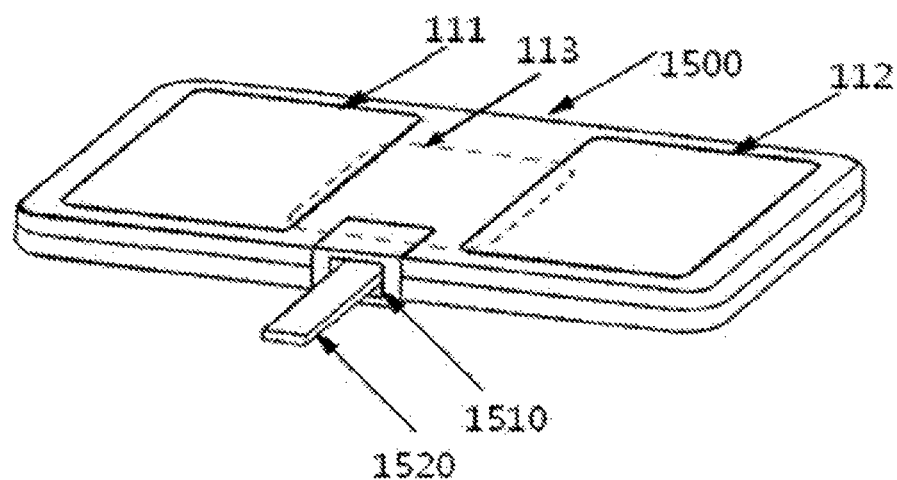
FIG. 15 shows an electrocardiogram measurement apparatus according to the present invention provided with a blood test strip insert port

As described above, the electrocardiogram measurement apparatus 100 according to the present invention may further include a function of measuring blood properties. In this case, one embodiment of the electrocardiogram measurement apparatus 1500 to which the function of measuring blood properties is added according to the present invention includes a blood property test strip insert port 1510 through which a blood property test strip 1520 can be inserted, and one type thereof may be configured as shown in FIG. 15.

The electrocardiogram measurement apparatus 100 according to the present invention has been described as being implemented in a plate shape. However, the electrocardiogram measurement apparatus according to the present invention uses the minimum number of filters in principle and has a simple circuit configuration, and accordingly it can be manufactured in a compact size. Accordingly, the electrocardiogram measurement apparatus according to the present invention has a feature that the power consumption of the battery is low. Accordingly, the electrocardiogram measurement apparatus according to the present invention is suitable to be implemented as a watch or ring shape. Particularly, when the electrocardiogram measurement apparatus according to the present invention is implemented as a watch shape or a ring shape, it is suitable for a user to always wear and has an advantage that it can be used in conjunction with a photoplethysmograph (PPG).

The PPG uses LEDs to emit light to the skin and measure reflected or transmitted light. Recently, the PPG built in the smart watch can provide heart rate, heart rate variability (HRV), and breathing rate (BR). HRV provides a lot of information about personal health conditions. HRV is used for sleep analysis or stress analysis, and is also used to detect arrhythmias such as atrial fibrillation. Normally, HRV analysis is performed using ECG. However, recently, it has also been performed using PPG. The PPG included in a patient monitor used in hospitals measures oxygen saturation and generates an alarm when the oxygen saturation is low. Recently, a PPG signal is obtained using a camera installed in a smartphone, and the occurrence of an arrhythmia symptom may be detected using the signal. Accordingly, PPG installed on the watch or ring facilitates detection of occurrence of an arrhythmia symptom. Accordingly, when the PPG and the electrocardiogram measurement apparatus according to the present invention are installed together on a watch or ring, the PPG may generate an alarm signal upon detecting occurrence of arrhythmia symptoms, and the user who receives the alarm signal can measure the electrocardiogram using the electrocardiogram measurement apparatus according to the present invention.

For user convenience and accuracy of ECG measurement, the locations of the electrocardiogram electrodes are important. A plurality of examples of implementing the electrocardiogram measurement apparatus according to the present invention on a watch will be described with reference to FIG. 16.

Figure 16:
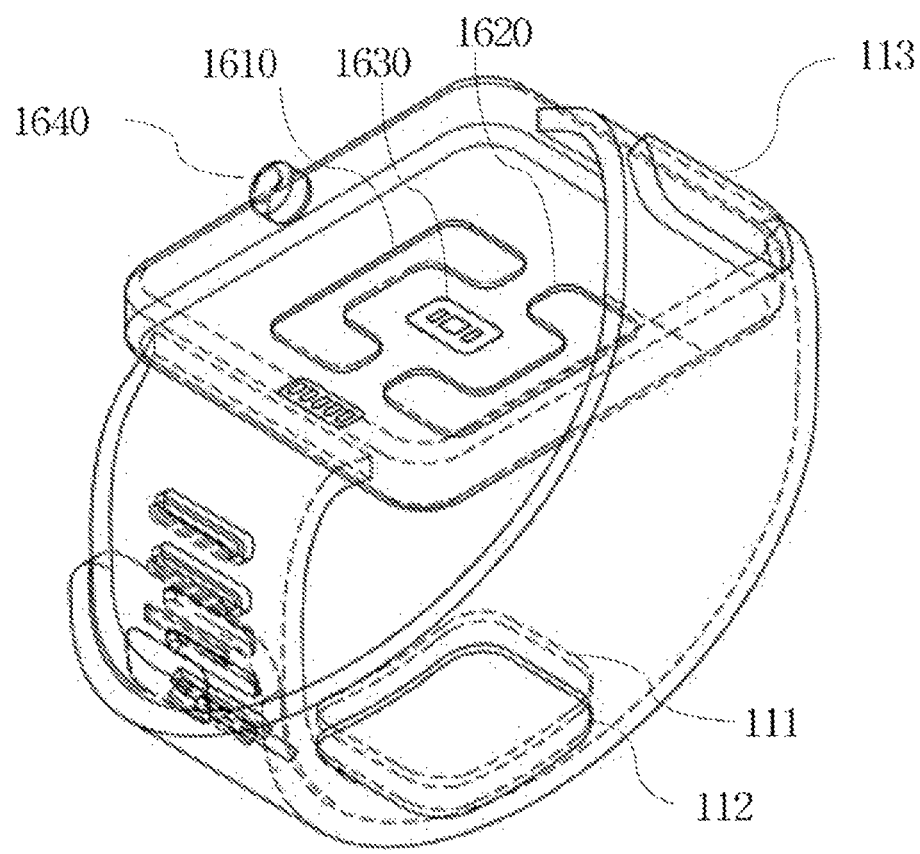
FIG. 16 shows an example of implementing the electrocardiogram measurement apparatus according to the present invention in the form of a smart watch.

In the first example, three ECG electrodes may be installed on both sides of a watch band. In FIG. 16, one ECG electrode 111 is installed on the inner surface of the band, i.e., the surface of the band contacting the wrist, and the two electrodes 112 and 113 are installed on the outer surface of the band, i.e., the surface of the band that does not contact the wrist. In this example, when the user wears the watch on the left wrist, the electrode 111 contacts the left wrist. In this case, the user brings the electrode 112 into contact with the left lower abdomen or chest and the right hand finger into contact with the electrode 113 to perform ECG measurement.

In the second example, one ECG electrode 1610 may be installed on the bottom surface of the watch. In this case, the electrode 1610 is always in contact with the wrist wearing the watch. When the user is to measure the ECG, the electrode 112 is brought into contact with the left lower abdomen or chest, and the electrode 113 is brought into contact with one finger of the hand without the watch.

In the third example, another part of the watch body, for example 1640, may be used instead of the electrode 113 of FIG. 16.

In all the above cases where electrodes are installed on a watch or watch band for user convenience and accuracy of electrocardiogram measurement, it should be noted that one electrode 112 is installed on the outer surface, that is, the surface of the band that does not contact the wrist, of a portion of the band located on the inside of the wrist (the palm side, not the back side of the hand). This is intended to make the electrode 112 comfortably contact the user's left lower abdomen or chest portion. In addition, in all the above cases where electrodes are installed on a watch or watch band, the PPG 1630 installed on the bottom surface of the watch may analyze the PPG signal and generate an alarm to the user.

Figure 17:
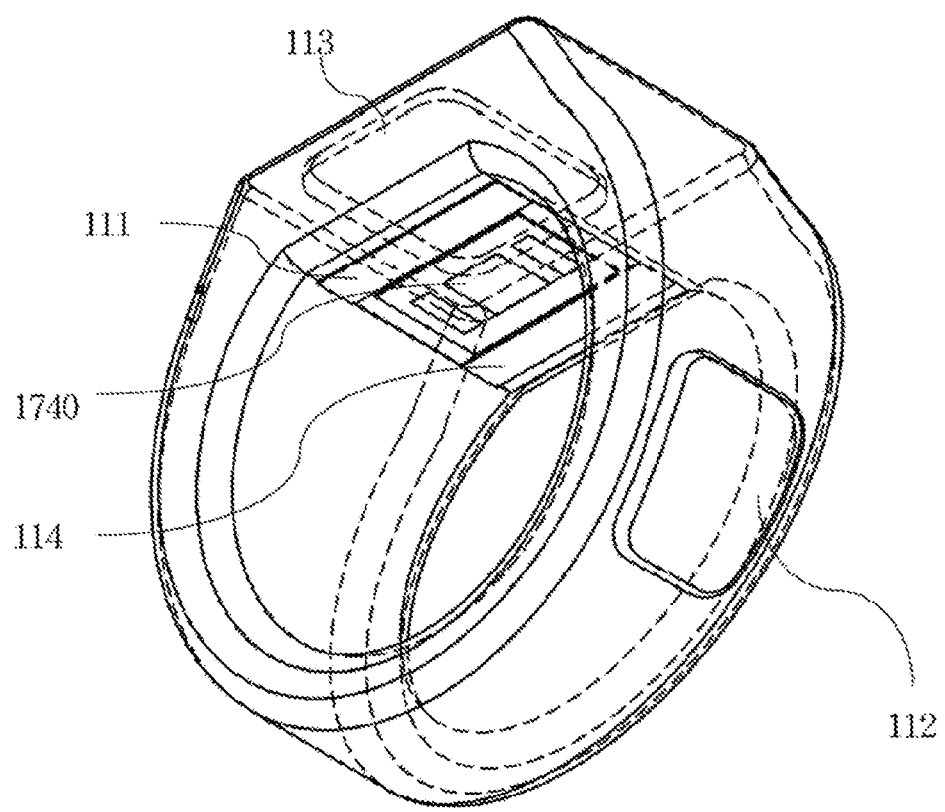
FIG. 17 shows an example of implementing the electrocardiogram measurement apparatus according to the present invention in the form of a ring.

The electrocardiogram measurement apparatus according to the present invention may be implemented in a ring shape. In this case, the ring is worn on the thumb or little finger to facilitate electrocardiogram measurement. FIG. 17 shows an example in which the electrocardiogram measurement apparatus according to the present invention is implemented in a ring shape. In FIG. 17, one electrode 111 among the three electrodes contacts a finger wearing the ring. The electrode 112 and electrode 113 are not in contact with the finger. That is, the electrode 112 and the electrode 113 are located on the outer portion of the thumb or little finger, and are arranged spaced apart from each other. When the ring is worn on the thumb of the left hand, the electrode 111 may be brought into contact with the thumb of the left hand, the electrode 112 may be brought into contact with the lower left abdomen, and the electrode 113 may be brought into contact with the second finger of the right hand. PPG 1730 installed on the surface of the ring that touches the skin may analyze the PPG signal and generate an alarm to the user.

Figure 18:
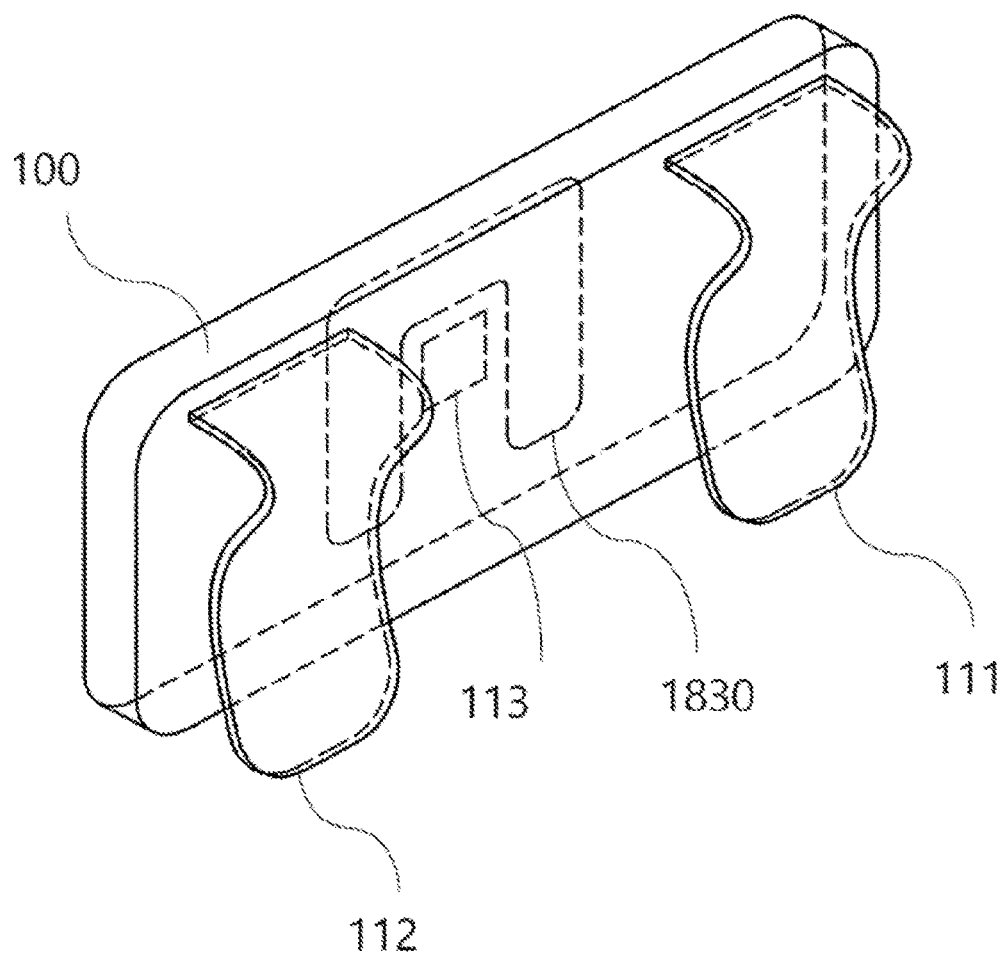
FIGS. 18 and 19 show examples of the electrocardiogram measurement apparatus configured to be coupled to pants to measure an electrocardiogram according to the present invention.
Figure 19:
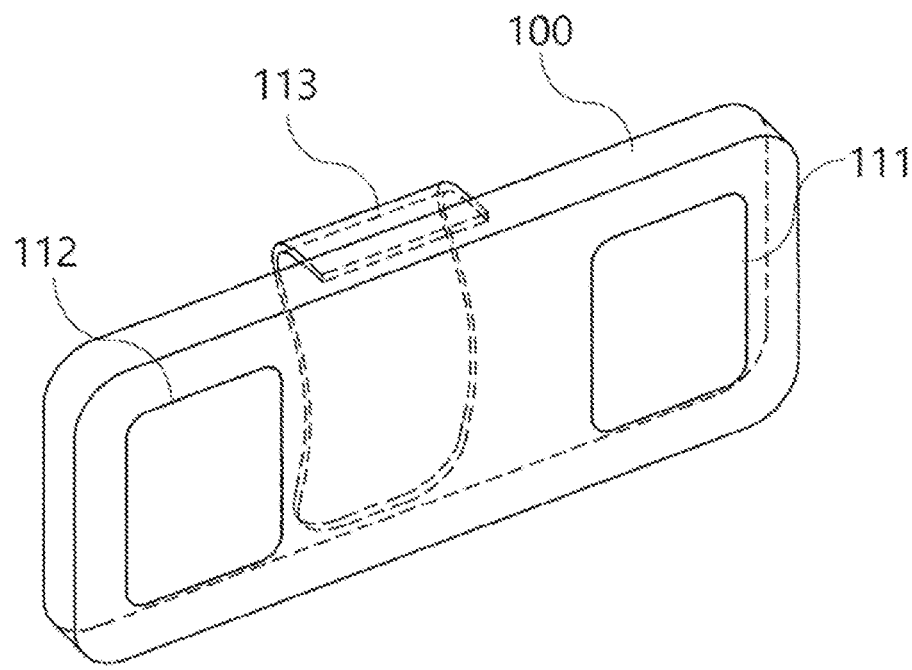

The electrocardiogram measurement apparatus according to the present invention may be implemented in a form that is easy to be coupled to other objects to keep the apparatus worn on a body. FIGS. 18 and 19 show examples of the electrocardiogram measurement apparatus according to the present invention that can be coupled to pants and measure an electrocardiogram immediately when the electrocardiogram is be measured. In FIG. 18, two clips 111 and 112 serving as two electrodes are used to attach the electrocardiogram measurement apparatus 100 according to the present invention to the inside of the pants, that is, between the pants and the user's body. When used, the electrocardiogram measurement apparatus 100 is attached to the pants at the position of the lower left abdomen using the clips 111 and 112. Then, the electrode 113 and the PPG 1830 automatically contact the lower left abdomen of the user. When the PPG 1830 sends an alarm or ECG measurement is needed, the user brings a left hand finger into contact with the clip 111 and brings a right hand finger into contact with the clip 112.

The electrocardiogram measurement apparatus 100 according to the present invention shown in FIG. 19 is attached to the outside of the pants. The electrocardiogram measurement apparatus 100 and the clip 113 inside the pants press the pants, and thus the electrocardiogram measurement apparatus 100 is fixed to the pants. When the electrocardiogram is measured, the clip 113 automatically contacts the user's lower left abdomen, and the user brings a left hand finger into contact with the electrode 111 and brings a right hand finger into contact with the electrode 112.

Figure 20:
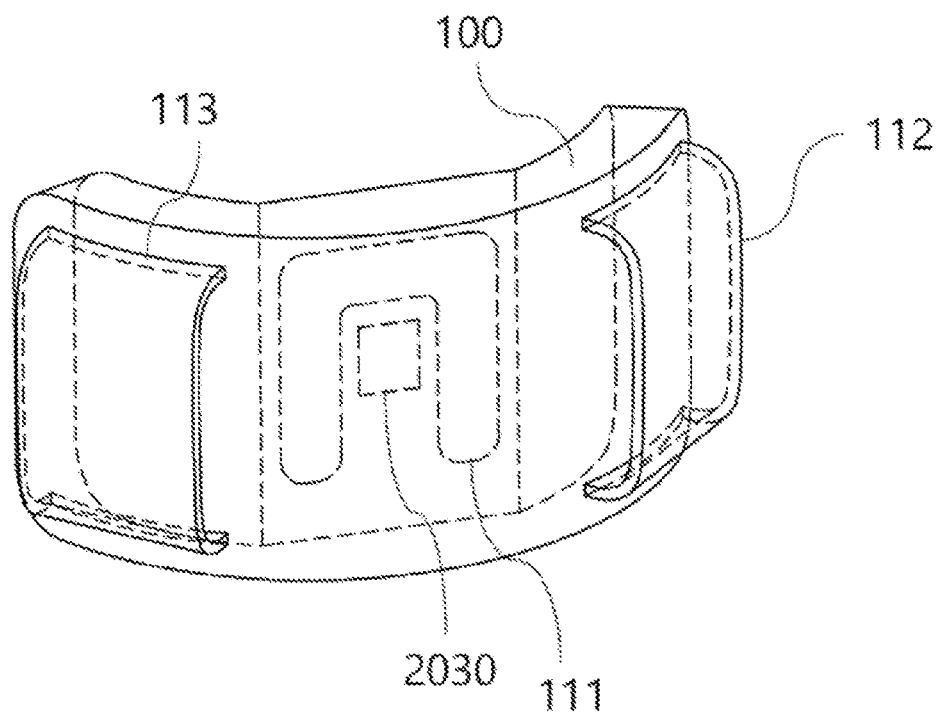
FIGS. 20 and 21 show embodiments of the electrocardiogram measurement apparatus that can be coupled to the band of a watch using two or one slide guide that serves as two or one electrode according to the present invention.
Figure 21:
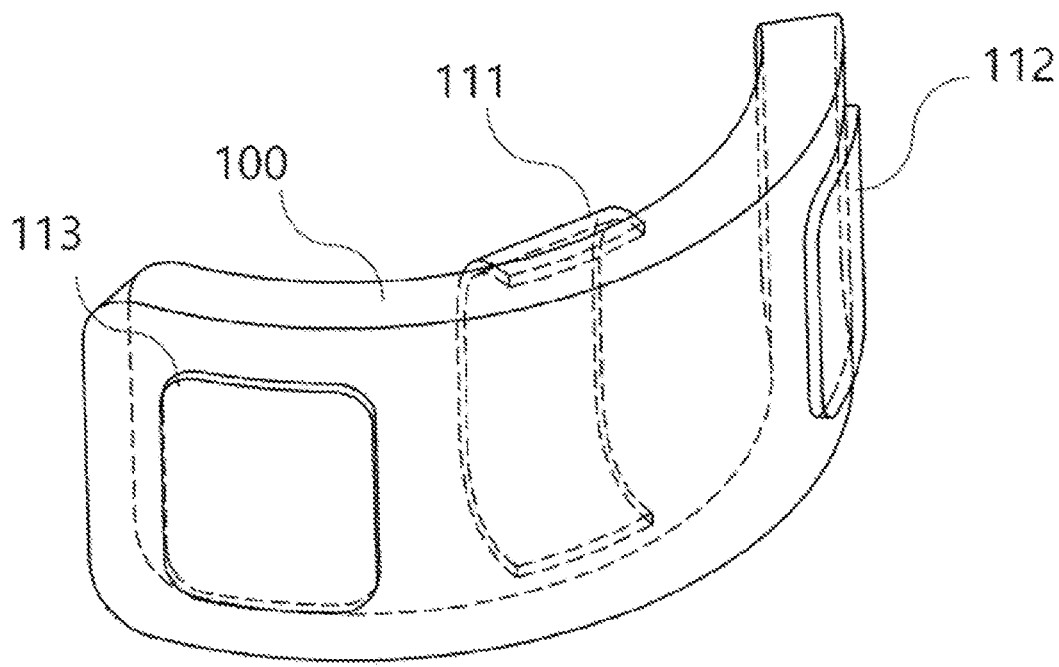

FIGS. 20 and 21 show embodiments of the electrocardiogram measurement apparatus that can be coupled to the band of a watch using two or one slide guide that serves as an electrode according to the present invention. In FIG. 20, when a watch band is inserted between the electrocardiogram measurement apparatus 100 according to the present invention and the slide guides 112 and 113 serving as electrodes, the electrocardiogram measurement apparatus 100 is fixed to the watch band. When the watch is worn on the left hand, the electrode 111 and the PPG 2030 automatically contact the left wrist. When the PPG 2030 sends an alarm or ECG measurement is needed, the user brings the lower left abdomen into contact with the slide guide 113 and brings a right hand finger into contact with the slide guide 112.

In FIG. 21, when the band of the watch is inserted between the electrocardiogram measurement apparatus 100 according to the present invention and the slide guide 111, the electrocardiogram measurement apparatus 100 is fixed to the band of the watch. When the watch is worn on the left hand, the electrode 111 automatically contacts the left wrist. In order to measure the ECG, the user brings the lower left abdomen into contact with the electrode 113 and brings a right hand finger into contact with the electrode 112.

As described above, the electrocardiogram measurement apparatus according to the present invention to which the PPGs 1830 and 2030 of FIGS. 18 and 20 are added is capable of constantly monitoring a user's heart rate. Although a separate drawing is not added for simplicity, it is apparent that the electrocardiogram measurement apparatus according to the present invention can be coupled to the band of a watch using the clips shown in FIG. 18 or 19 instead of the slide guides shown in FIGS. 20 and 21.

In the embodiment of the electrocardiogram measurement apparatus according to the present invention, the electrocardiogram measurement apparatus 100 is described as including three electrodes. However, in another embodiment according to the present invention, the electrocardiogram measurement apparatus may include four electrodes. The operation principle of an electrocardiogram measurement apparatus including the four electrodes according to the present invention is the same as that of the previous case of including three electrodes. The important point is that the electrocardiogram measurement apparatus including four electrodes according to the present invention includes three amplifiers configured to receive an ECG signal from three electrodes, the three amplifiers each amplify one ECG signal, and accordingly the apparatus actually measures three ECG signals simultaneously.

Figure 22:
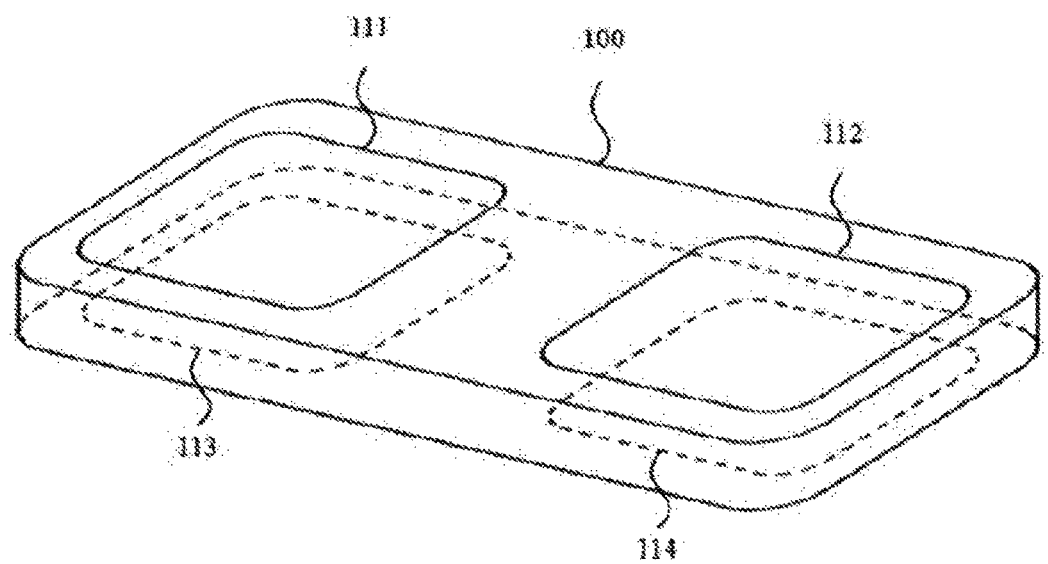
FIG. 22 is a perspective view of an electrocardiogram measurement apparatus having four electrodes according to the present invention.

The electrocardiogram measurement apparatus including the four electrodes may be easily implemented by the foregoing description. The method of using the electrocardiogram measurement apparatus including the four electrodes according to the present invention is almost the same as the method of using the electrocardiogram measurement apparatus 100 including the three electrodes according to the present invention. The three ECG signals measured by the electrocardiogram measurement apparatus including four electrodes according to the present invention include, for example, two limb leads and one MCL. Alternatively, the three ECG signals may be one limb lead and two MCLS. An embodiment of the electrocardiogram measurement apparatus including the four electrodes according to the present invention is illustrated in FIG. 22. In FIG. 22, the four electrodes 111, 112, 113, and 114 are provided on two plate-shaped wide surfaces, two on each wide surface.

The electrocardiogram measurement apparatus according to the present invention has been described in detail, but the present invention is not limited thereto.

The present invention may be changed in various forms according to the intention of the present invention.

INDUSTRIAL APPLICABILITY

An electrocardiogram measurement apparatus according to the present invention can be used as a portable electrocardiogram measurement apparatus that is convenient to carry and easy to use regardless of time and place while it provides multi-channel electrocardiogram information.

The invention claimed is:

1. An electrocardiogram measurement apparatus, comprising:
a first electrode and a second electrode configured to receive two electrocardiogram voltages of a body part in contact therewith, respectively;
two amplifiers configured to receive the two electrocardiogram voltages from the first electrode and the second electrode, respectively;
one electrode driver configured to output a driving voltage;
a third electrode configured to receive the output of the electrode driver and transmit the output of the electrode driver to the body part in contact therewith;
an AD converter connected to an output terminal of each of the two amplifiers to convert output signals of the two amplifiers into two digital signals;
a microcontroller configured to receive the two digital signals of the AD converter; and
a communication means configured to transmit the two digital signals,
wherein:
the microcontroller is supplied with power from a battery;
the microcontroller controls the AD converter and the communication means;
the two amplifiers each receive and amplify one electrocardiogram voltage simultaneously; and
an output impedance of the electrode driver is less than an input impedance of each of the two amplifiers.

2. The electrocardiogram measurement apparatus of claim 1, wherein the two amplifiers are single-ended input amplifiers.

3. The electrocardiogram measurement apparatus of claim 1, wherein one of the two amplifiers is a differential amplifier and the other one is a single-ended input amplifier.

4. The electrocardiogram measurement apparatus of claim 1, wherein the electrode driver is a band pass filter having a resonance frequency equal to a frequency of an external power line.

5. The electrocardiogram measurement apparatus of claim 1, wherein the electrode driver is a constant voltage generator.

6. The electrocardiogram measurement apparatus of claim 1, wherein the electrocardiogram measurement apparatus is plate-shaped,
wherein first and second electrodes of the three electrodes are arranged spaced apart from each other by a predetermined distance in a longitudinal direction on one surface of a case of the electrocardiogram measurement apparatus so as to be brought into contact with both hands of a user by the user, and a third electrode is arranged on an opposite surface of the case.

7. The electrocardiogram measurement apparatus of claim 6, further comprising:
a blood property measurement unit configured to measure blood properties (one or more of blood glucose level, ketone level, or INR).

8. The electrocardiogram measurement apparatus of claim 6, further comprising:
a body temperature measurement unit configured to measure a body temperature.

9. The electrocardiogram measurement apparatus of claim 6, further comprising:
a current detector configured to cause minute current to flow when a plurality of electrodes are brought into contact with a human body and to generate an output by detecting the minute current.

10. The electrocardiogram measurement apparatus of claim 6, wherein the communication means supports Bluetooth low energy (BLE).

11. The electrocardiogram measurement apparatus of claim 1, wherein the two electrocardiogram voltages are two limb lead signals,
wherein four limb lead signals are additionally obtained using the two limb lead signals.

12. The electrocardiogram measurement apparatus of claim 1, wherein the two electrocardiogram signals are one limb lead and one MCL.

13. The electrocardiogram measurement apparatus of claim 1, wherein the electrocardiogram measurement apparatus and the three electrodes are installed on a watch or watch band,
wherein one of the three electrodes is installed on an outer surface (surface not contacting the wrist) of a portion of the band, the portion being located on an inside of a wrist (a palm side, not a back side of a corresponding hand).

14. The electrocardiogram measurement apparatus of claim 1, wherein the electrocardiogram measurement apparatus and the three electrodes are installed on a ring worn on a thumb or a little finger,
   wherein one of the three electrodes contacts the ring wearing finger, and the other two electrodes are installed on an outer portion not in contact with the finger, and
   wherein the two electrodes are arranged spaced apart from each other.

15. The electrocardiogram measurement apparatus of claim 1, wherein the electrocardiogram measurement apparatus is attached to pants by one or two clips serving as one or two electrodes.

16. The electrocardiogram measurement apparatus of claim 1, wherein the electrocardiogram measurement apparatus is attached to a watch band by one or two clips or slide guides serving as one or two electrodes.

17. An electrocardiogram measurement apparatus, comprising:
   a first electrode, a second electrode and a third electrode configured to receive three electrocardiogram voltages of a body part in contact therewith, respectively;
   three amplifiers configured to receive the three electrocardiogram voltages from the first electrode, the second electrode, and the third electrode, respectively;
   an electrode driver configured to output a driving voltage;
   a fourth electrode configured to receive the output of the electrode driver and transmit the output of the electrode driver to the body part in contact therewith;
   an AD converter connected to an output terminal of each of the three amplifiers to convert output signals of the three amplifiers into three digital signals;
   a microcontroller configured to receive the three digital signals of the AD converter; and
   a communication means configured to transmit the three digital signals,
   wherein:
   the microcontroller is supplied with power from a battery;
   the microcontroller controls the AD converter and the communication means;
   the three amplifiers each receive and amplify one electrocardiogram voltage simultaneously; and
   an output impedance of the electrode driver is less than an input impedance of each of the three amplifiers.

* * * * *

UNITED STATES PATENT AND TRADEMARK OFFICE
CERTIFICATE OF CORRECTION

| | |
|---|---|
| PATENT NO. | : 11,589,793 B2 |
| APPLICATION NO. | : 16/768769 |
| DATED | : February 28, 2023 |
| INVENTOR(S) | : In-Duk Hwang |

It is certified that error appears in the above-identified patent and that said Letters Patent is hereby corrected as shown below:

On the Title Page

In item (73), under "Assignee", in Column 1 Line 3, delete "WELLBEINGSOFT INC., Daejeon (KR)" and insert --HEXACHECK INC., Daejeon (KR)-- in its place.

Signed and Sealed this
Eighth Day of August, 2023

Katherine Kelly Vidal
*Director of the United States Patent and Trademark Office*